US012742058B2

(12) United States Patent
Knerr et al.

(10) Patent No.: US 12,742,058 B2
(45) Date of Patent: Sep. 22, 2026

(54) ULTRAFINE SURFACE-TREATED FILLERS FOR THIN BREATHABLE FILMS

(71) Applicant: OMYA INTERNATIONAL AG, Oftringen (CH)

(72) Inventors: Michael Knerr, Oftringen (CH); Christoph Hirsiger, Koppigen (CH)

(73) Assignee: OMYA INTERNATIONAL AG, Oftringen (CH)

( * ) Notice: Subject to any disclaimer, the term of this patent is extended or adjusted under 35 U.S.C. 154(b) by 646 days.

(21) Appl. No.: 18/252,411

(22) PCT Filed: Nov. 25, 2021

(86) PCT No.: PCT/EP2021/083033
§ 371 (c)(1),
(2) Date: May 10, 2023

(87) PCT Pub. No.: WO2022/112434
PCT Pub. Date: Jun. 2, 2022

(65) Prior Publication Data

US 2023/0416499 A1 Dec. 28, 2023

(30) Foreign Application Priority Data

Nov. 25, 2020 (EP) .................................... 20209918

(51) Int. Cl.
*C08K 9/04* (2006.01)
*A61L 15/22* (2006.01)
*A61L 15/42* (2006.01)
*C08J 5/18* (2006.01)
*C08K 3/26* (2006.01)
*C09C 1/02* (2006.01)

(52) U.S. Cl.
CPC .............. *C08K 9/04* (2013.01); *A61L 15/225* (2013.01); *A61L 15/42* (2013.01); *C08J 5/18* (2013.01); *C08K 3/26* (2013.01); *C09C 1/021* (2013.01); *C08J 2323/06* (2013.01); *C08K 2003/265* (2013.01); *C08K 2201/003* (2013.01); *C08K 2201/005* (2013.01); *C08K 2201/006* (2013.01)

(58) Field of Classification Search
CPC ...... C08K 9/04; C08K 3/26; C08K 2003/265; C08K 2201/003; C08K 2201/005; C08K 2201/006; A61L 15/225; A61L 15/42; C08J 5/18; C08J 2323/06; C09C 1/021
USPC .......................................................... 523/111
See application file for complete search history.

(56) References Cited

U.S. PATENT DOCUMENTS

| | | | | |
|---|---|---|---|---|
| 2012/0031576 A1 | | 2/2012 | Gane et al. | |
| 2018/0230312 A1* | | 8/2018 | Rentsch | C09C 1/021 |
| 2022/0089846 A1* | | 3/2022 | Koplin | B29C 49/0005 |

FOREIGN PATENT DOCUMENTS

| | | | | |
|---|---|---|---|---|
| EP | 2070991 | A1 | 6/2009 | |
| EP | 2264108 | A1 | 12/2010 | |
| EP | 2264109 | A1 | 12/2010 | |
| EP | 2371766 | A1 | 10/2011 | |
| EP | 2447213 | A1 | 5/2012 | |
| EP | 2524898 | A1 | 11/2012 | |
| EP | 2840065 | A1 | 2/2015 | |
| EP | 2975078 | A1 * | 1/2016 | C08J 5/18 |
| EP | 3176204 | A1 | 6/2017 | |
| EP | 3339355 | A1 | 6/2018 | |
| EP | 3572456 | A1 * | 11/2019 | B32B 27/28 |
| WO | 03/050167 | A1 | 6/2003 | |
| WO | 2009/074492 | A1 | 6/2009 | |
| WO | 2013/142473 | A1 | 9/2013 | |
| WO | 2014/060286 | A1 | 4/2014 | |
| WO | 2018/095909 | A1 | 5/2018 | |

OTHER PUBLICATIONS

International Search Report from PCT/EP2021/083033, mailed Mar. 2, 2022, 4 pages.
Written Opinion from PCT/EP2021/083033, mailed Mar. 2, 2022, 8 pages.

* cited by examiner

*Primary Examiner* — Robert S Jones, Jr.
*Assistant Examiner* — Elizabeth Amato
(74) *Attorney, Agent, or Firm* — ALGM LLP; Harry J. Guttman

(57) ABSTRACT

The present invention relates to a breathable film having a basis weight from 1 to 15 g/m$^2$ comprising at least one thermoplastic polymer and a surface-treated filler material comprising calcium carbonate. The surface-treated filler material has a specific particle size distribution and a specific surface-treatment layer. The present invention further relates to a process for producing the breathable film, the use of a surface-treated filler material comprising calcium carbonate as a filler in a breathable film, an article comprising the breathable film and uses of the breathable film.

21 Claims, No Drawings

ULTRAFINE SURFACE-TREATED FILLERS FOR THIN BREATHABLE FILMS

The present invention relates to a breathable film having a basis weight from 1 to 15 g/$m^2$ comprising at least one thermoplastic polymer and a surface-treated filler material comprising calcium carbonate, a process for producing the breathable film, the use of a surface-treated filler material comprising calcium carbonate as a filler in a breathable film, an article comprising the breathable film and uses of the breathable film.

The first breathable films for hygiene products were developed as early as 1983 in Japan. Production of breathable films began in the USA in the mid-1990s and later in Europe, where they rapidly commanded a large market share.

Breathable films typically comprise a blend of thermoplastic polymers and an inorganic filler such as calcium carbonate and are produced by forming a film from said blend by casting or blowing with subsequent stretching of the film. The stretching process delaminates the polymer from the surface of the inorganic filler particles, which produces micropores, often referred to as "voids" in the film's cross section, which allows the passage of water vapour during end-use. At the same time, the micropores of the breathable film remain small enough to prevent the penetration of liquid water.

Application EP2975078 A1 discloses a surface-treated filler for breathable films, comprising at least one mono-substituted succinic anhydride and/or at least one mono-substituted succinic acid and/or salty reaction product(s) thereof and a ground calcium carbonate-comprising filler material.

European patent application EP3176204 A1 discloses a surface-treated filler for an ultrathin breathable film, comprising a surface-treatment layer based on phosphoric acid ester blends, aliphatic carboxylic acids, aliphatic aldehydes, polydialkylsiloxanes or mixtures thereof and a fine ground calcium carbonate-comprising filler material.

Application WO03050167 A1 relates to a breathable film comprising a ground particulate calcium carbonate material having a $d_{50}$ of less than 1.0 μm and comprising an aliphatic carboxylic acid coating.

Currently, breathable films have two main fields of application: personal hygiene products, such as infant diapers, feminine hygiene pads (napkins, panty liners) or adult incontinence products, and construction industry, such as under-roofing membranes, house wraps or wall coverings.

However, the specific permeability properties of these films also have uses in other industries, such as disposable clothing in medical and industrial applications.

Since breathable films are produced in large amounts for products that are disposed of after a single use, it is highly desirable to reduce the film thickness in order to save materials, which reduces costs and improves the sustainability of the processes. At the same time, the breathability and the penetration resistance must not be compromised, so that the breathable films remain suitable for their intended applications. Likewise, instable film formation processes, indicated by nozzle deposits, pressure build-up in the extruder, film defects or even film ruptures, have to be avoided. Film defects are indicated, e.g., by the presence of agglomerated inorganic fillers or holes. Furthermore, thin breathable films can be hardly prepared without deteriorating its mechanical properties such as maximum tensile force, elongation at break or modulus of elasticity and the surface quality of the films.

Thus, the present inventors were faced with the multifaceted problem of providing a breathable film having a reduced thickness, or reduced basis weight, which maintains the required breathability and resistance to liquid penetration. At the same time, the mechanical properties of the film should be maintained or even improved; and the breathable film should be produced by a stable process.

Accordingly, it is an object of the present invention to provide a thin breathable film having a reduced thickness, or reduced basis weight, which maintains the required breathability and resistance to liquid penetration. At the same time, the mechanical properties of the film should be maintained or even improved; and the breathable film should be produced by a stable process.

The foregoing objects and other objects are solved by the subject-matter as defined herein in the independent claims.

One aspect of the present invention relates to a breathable film having a basis weight from 1 to 15 g/$m^2$. The breathable film comprises at least one thermoplastic polymer and a surface-treated filler material, wherein the surface-treated filler material comprises A) at least one calcium carbonate-comprising filler material having
   - a weight median particle size $d_{50}$ in the range from 0.1 μm to 7 μm,
   - a top cut particle size $d_{98}$ of ≤15 μm,
   - a fineness (<0.5 μm) such that at least 15 wt.-% of all particles have a particle size of <0.5 μm, and
   - a residual total moisture content of ≤1 wt.-%, based on the total dry weight of the at least one calcium carbonate-comprising filler material, and B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

The present inventors found that the combination of at least one calcium carbonate-comprising filler material having a specific particle size distribution, as defined by the $d_{50}$, the $d_{98}$ and the fineness (<0.5 μm), with a treatment layer comprising at least one mono-substituted succinic anhydride and/or at least one mono-substituted succinic acid and/or salty reaction product(s) thereof, yields a surface-treated filler material, which allows for obtaining a thin breathable film having the desired properties by a stable manufacturing process. The particle size distribution of the surface-treated filler material allows for reliably inducing the desired micropores when the film is stretched in at least one direction. At the same time, the amount of film defects is minimized. Furthermore, due to the defined specific particle size distribution and fineness of the calcium carbonate-comprising filler it is possible to prepare thinner films since the thickness of the films is limited by the particle size of the filler material. The inventors realized that the inventive treatment layer is crucial for evenly dispersing the particles within the polymer matrix, which is not possible using, e.g., surface-treatment agents based on fatty acids or salts thereof since such surface treatment agents result in aggregates.

According to a second aspect of the present invention, a process for producing the breathable film having a basis weight from 1 to 15 g/$m^2$ is provided. The process comprises the steps of:

a) providing a composition comprising at least one thermoplastic polymer and a surface-treated filler material, and b) forming a film from the composition of step a), and c) stretching the film obtained in step b) in at least one direction, wherein the surface-treated filler material comprises A) at least one calcium carbonate-comprising filler material having a weight median particle size $d_{50}$ in the range from 0.1 μm to 7 μm, a top cut particle size $d_{98}$ of ≤15 μm, a fineness (<0.5 μm) such that at least 15 wt.-% of all particles have a particle size of <0.5 μm, and a residual total moisture content of ≤1 wt.-%, based on the total dry weight of the at least one calcium carbonate-comprising filler material, and B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

A third aspect of the present invention relates to the use of a surface-treated filler material as a filler in a breathable film having a basis weight from 1 to 15 g/m$^2$, the breathable film comprising at least one thermoplastic polymer, wherein the surface-treated filler material comprises A) at least one calcium carbonate-comprising filler material having a weight median particle size $d_{50}$ in the range from 0.1 μm to 7 μm, a top cut particle size $d_{98}$ of ≤15 μm, a fineness (<0.5 μm) such that at least 15 wt.-% of all particles have a particle size of <0.5 μm, and a residual total moisture content of ≤1 wt.-%, based on the total dry weight of the at least one calcium carbonate-comprising filler material, and B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

Preferably, the water vapour retention rate and/or the hydrostatic pressure and/or the machinability of the breathable film is improved, compared to the same breathable film comprising a surface-treated filler material, which comprises the at least one calcium carbonate-comprising filler material and a treatment layer on the surface of the at least one calcium carbonate-comprising filler material comprising at least one saturated aliphatic linear or branched monocarboxylic acid and salty reaction products thereof, wherein the water vapour retention rate is determined according to ASTM E398-20, the hydrostatic pressure is determined according to AATCC Test Method 127-2013, WSP 80.6 or DIN EN ISO 811:2018-08, and the machinability is measured as a pressure increase observed in an extruder when producing the breathable film for 1 h and 5 min, wherein the pressure increase is measured by producing the breathable film by extruding a composition comprising the surface-treated filler material and the at least one thermoplastic polymer in a single screw extruder having a temperature profile of 195° C.-210° C.-230° C.-230° C., a screw diameter of 30 mm, a rotation speed of the extruder screw of 35 rpm and a die gap of 0.85 mm, wherein the pressure increase is defined as the difference of the initial pressure and the final pressure, measured in the extruder before the melt filter, wherein the initial pressure is measured 5 minutes after a melt filter with 42 micron mesh size is placed against the breaker plate between the extruder screw tip and the die, and wherein the final pressure is measured after 1 h and 5 min of producing the breathable film.

The present inventors found that the use of the inventive surface-treated filler material in the breathable film allows for improving, i.e., increasing the breathability of the film, as measured by the water vapour transmission rate. Furthermore, the inventive surface-treated filler material improves, i.e., increases, the resistance to liquid penetration, as indicated by the hydrostatic pressure. In addition, the inventive surface-treated filler material improves the machinability of the breathable film, i.e., improves the stability of the production process, as indicated by a low or negligible pressure increase in an extruder, measured as described herein. Additionally or alternatively, the inventive surface-treated filler material allows for reducing the film thickness, i.e., the film grammage, while retaining the desired breathability, resistance to liquid penetration, mechanical properties and machinability of the breathable films.

In a fourth aspect of the present invention, an article comprising the inventive breathable film having a basis weight from 1 to 15 g/m$^2$ is provided. The article is selected from the group consisting of hygiene products, medical products, healthcare products, filter products, geotextile products, agriculture products, horticulture products, clothing, footwear products, baggage products, household products, industrial products, packaging products, building products, and construction products.

A fifth aspect of the present invention relates to the use of the inventive breathable film having a basis weight from 1 to 15 g/m$^2$ in hygienic applications, medical applications, healthcare applications, filtration materials, geotextile products, agricultural applications, horticultural applications, clothing, footwear products, baggage products, household applications, industrial applications, packaging applications, building applications, or construction.

Advantageous embodiments of the present invention are defined herein and also in the corresponding dependent claims.

In one embodiment of any one of the aspects of the present invention, the at least one calcium carbonate-comprising filler material is natural ground calcium carbonate, precipitated calcium carbonate, surface-reacted calcium carbonate, or a mixture thereof, and preferably natural ground calcium carbonate.

In another embodiment of any one of the aspects of the present invention, the at least one thermoplastic polymer is a polyolefin, preferably selected from the group consisting of polypropylene, polyethylene, polybutylene, and mixtures thereof, and more preferably selected from the group consisting of high density polyethylene (HDPE), linear low density polyethylene (LLDPE), low density polyethylene (LDPE), ultra-low density polyethylene (ULDPE), very low density polyethylene (VLDPE), and mixtures thereof.

In still another embodiment of any one of the aspects of the present invention, the breathable film comprises the surface-treated filler material in an amount from 1 to 85 wt.-%, based on the total weight of the breathable film, preferably from 2 to 80 wt.-%, more preferably from 5 to 75 wt.-%, even more preferably from 10 to 65 wt.-%, and most preferably from 15 wt.-% to 60 wt.-%.

In yet another embodiment of any one of the aspects of the present invention, the at least one calcium carbonate-comprising filler material has a) a weight median particle size $d_{50}$ from 0.25 μm to 5 μm, preferably from 0.5 μm to 4 μm, and most preferably from 0.6 μm to 1 μm, and/or b) a top cut particle size $d_{98}$ of ≤12.5 μm, preferably of ≤10 μm, more preferably of ≤7.5 μm, and most preferably of ≤3 μm, and/or c) a fineness (<1 μm) such that at least 70 wt.-%, even more preferably at least 75 wt.-% and most preferably at least 80 wt.-% of all particles have a particle size of ≤1 μm, and/or d) a fineness (<0.5 μm) such that at least 20 wt.-%, preferably at least 25 wt.-%, and most preferably at least 30 wt.-% of all particles have a particle size of <0.5 μm.

In one embodiment of any one of the aspects of the present invention, the at least one calcium carbonate-comprising filler material has a specific surface area (BET) of from 0.5 to 150 $m^2/g$, preferably of from 1 to 50 $m^2/g$, more preferably of from 2 to 35 $m^2/g$, and most preferably of from 4 to 15 $m^2/g$, as measured using nitrogen and the BET method according to ISO 9277:2010.

In another embodiment of any one of the aspects of the present invention, the at least one calcium carbonate-comprising filler material has a residual total moisture content of from 0.01 to 0.2 wt.-%, preferably from 0.02 to 0.15 wt.-%, and most preferably from 0.04 to 0.15 wt.-%, based on the total dry weight of the at least one calcium carbonate-comprising filler material.

In still another embodiment of any one of the aspects of the present invention, the surface-treated filler material has a moisture pick-up from 0.1 to 1 mg/g, preferably from 0.2 to 0.9 mg/g, and most preferably from 0.2 to 0.8 mg/g, at a temperature of 23° C. (±2° C.).

In yet another embodiment of any one of the aspects of the present invention, the at least one mono-substituted succinic anhydride consists of succinic anhydride mono-substituted with a group selected from a linear, branched, aliphatic or cyclic group having a total amount of carbon atoms from C2 to C30, preferably from C3 to C25, and most preferably from C4 to C20 in the substituent.

In one embodiment of any one of the aspects of the present invention, the film has a basis weight from 4 to 13 $g/m^2$, preferably from 6 to 12 $g/m^2$, more preferably from 7 to 10 $g/m^2$ and most preferably about 8 $g/m^2$.

In one embodiment of the process of the present invention, the composition provided in step a) is a masterbatch or a compound obtained by mixing and/or kneading the at least one thermoplastic polymer and the surface-treated filler material to form a mixture and continuously pelletizing the obtained mixture underwater.

It should be understood that for the purposes of the present invention, the following terms have the following meanings:

The term "breathable film" in the meaning of the present invention refers to a polymer film that allows the passage of gases and moisture vapour, for example, due to the presence of micropores. The "breathability" of a breathable film can be measured by its water vapour transmission rate (WVTR), which is specified in $g/(m^2 \cdot day)$. For example, a polymer film may considered as being "breathable" if it has a WVTR of at least 1 000 $g/(m^2 \cdot day)$. The WVTR may be determined with a Lyssy L80-5000 measuring device according to ASTM E398-20.

The term "thin" breathable film in the meaning of the present invention refers to a polymer film having a basis weight from 1 to 15 $g/m^2$, preferably from 1 to 13 $g/m^2$, more preferably from 4 to 13 $g/m^2$, even more preferably from 6 to 12 $g/m^2$, still more preferably from 7 to 10 $g/m^2$, and most preferably about 8 $g/m^2$. Breathable films having a basis weight of 10 $g/m^2$ or below in the meaning of the present invention are considered "ultrathin" breathable films.

A "film" in the meaning of the present invention is a sheet or layer of material having a median thickness which is small compared to its length and width. For example, the term "film" may refer to a sheet or layer of material having a median thickness of less than 200 μm, but not more than 1 μm.

The term "surface-treated filler material" in the meaning of the present invention refers to a material, which has been contacted with a surface-treatment agent such as to obtain a treatment layer (or coating layer) on at least a part of the surface of the calcium carbonate-comprising filler material, wherein the calcium carbonate-comprising filler material comprises at least 50 wt.-%, preferably at least 80 wt.-% calcium carbonate, based on the total dry weight of the calcium carbonate-comprising filler material.

The term "ground natural calcium carbonate" (GNCC) as used herein refers to a particulate material obtained from natural calcium carbonate-containing minerals, such as chalk, limestone, marble or dolomite, or from organic sources, such as eggshells or seashells, which has been processed in a wet and/or dry comminution step, such as crushing and/or grinding, and optionally has been subjected to further steps such as screening and/or fractionation, for example, by a cyclone or a classifier. "Ground natural calcium carbonate" may be "wet ground" or "dry ground", wherein a "wet ground natural calcium carbonate" in the meaning of the present invention is a ground natural calcium carbonate which has been manufactured by a process including at least one grinding step in aqueous suspension with a solids content between 20 and 80 wt.-% and a "dry ground natural calcium carbonate" is a ground natural calcium carbonate which has been manufactured by a process including at least one grinding step in aqueous suspension with a solids content of more than 80 and up to 100 wt.-%.

A "precipitated calcium carbonate" (PCC) in the present meaning is a synthesized material, obtained by precipitation following a reaction of carbon dioxide and calcium hydroxide (hydrated lime) in an aqueous environment. Alternatively, precipitated calcium carbonate can also be obtained by reacting calcium and carbonate salts, for example calcium chloride and sodium carbonate, in an aqueous environment. PCC may have a vateritic, calcitic or aragonitic crystalline form. PCCs are described, for example, in EP2447213 A1, EP2524898 A1, EP2371766 A1, EP2840065 A1, or WO2013142473 A1.

A "surface-reacted calcium carbonate" according to the present invention is a reaction product of ground natural calcium carbonate (GNCC) or precipitated calcium carbonate (PCC) treated with carbon dioxide and one or more $H_3O^+$ ion donors, wherein the carbon dioxide is formed in situ by the $H_3O^+$ ion donors treatment and/or is supplied from an external source. A $H_3O^+$ ion donor in the context of the present invention is a Brønsted acid and/or an acid salt.

The term "dry" calcium carbonate-comprising filler material is understood to be a filler material having less than 0.3% by weight of water relative to the filler material weight. The % water (equal to "residual total moisture content") is determined according to the Coulometric Karl Fischer measurement method, wherein the filler material is heated to 220° C., and the water content released as vapour and isolated using a stream of nitrogen gas (at 100 ml/min) is determined in a Coulometric Karl Fischer unit.

The "particle size" of the calcium carbonate-containing materials herein is described by its weight distribution of particle sizes $d_x$. Therein, the value $d_x$ represents the diameter relative to which x % by weight of the particles have diameters less than $d_x$. This means that, for example, the $d_{20}$ value is the particle size at which 20 wt.-% of all particles are smaller than that particle size. The $d_{50}$ value is thus the weight median particle size, i.e. 50 wt.-% of all particles are smaller than that particle size and the $d_{98}$ value, referred to as top cut, is the particle size at which 98 wt.-% of all particles are smaller than that particle size. The weight median particle size $d_{50}$ and top cut $d_{98}$ are measured by the sedimentation method, which is an analysis of sedimentation behaviour in a gravimetric field. The measurement is made with a Sedigraph™ 5120 of Micromeritics Instrument Corporation, USA. The method and the instrument are known to the skilled person and are commonly used to determine particle size distributions.

The "fineness (<0.5 μm)" of the calcium carbonate-containing materials refers to the amount of particles by weight having a particle size smaller than 0.5 μm. Likewise, the "fineness (<1 μm)" of the calcium carbonate-containing materials refers to the amount of particles by weight having a particle size smaller than 1 μm. The measurement is made with a Sedigraph™ 5120 of Micromeritics Instrument Corporation, USA. The method and the instrument are known to the skilled person and are commonly used to determine particle size distributions.

Throughout the present document, the term "specific surface area" (in $m^2/g$), which is used to define calcium carbonate or other materials, refers to the specific surface area as determined by using the BET method (using nitrogen as adsorbing gas), as measured according to ISO 9277:2010.

Unless indicated otherwise, the "residual total moisture content" of a material refers to the percentage of moisture (i.e. water) which may be desorbed from a sample upon heating to 220° C. The "residual total moisture content" is determined according to the Coulometric Karl Fischer measurement method, wherein the filler material is heated to 220° C., and the water content released as vapor and isolated using a stream of nitrogen gas (at 100 ml/min) is determined in a Coulometric Karl Fischer unit (e.g. Mettler-Toledo coulometric KF Titrator C30, combined with Mettler-Toledo oven DO 0337).

The term "moisture pick-up susceptibility" or "moisture pick-up" in the meaning of the present invention refers to the amount of moisture adsorbed on the surface of the powder material or surface-treated filler material and can be determined in mg moisture/g of the dry powder material or surface-treated filler material after exposure to an atmosphere of 10 and 85% of relative humidity, respectively, for 2.5 hours at a temperature of +23° C. (±2° C.).

The term "(total) dry weight of the calcium carbonate-containing filler material" is understood to describe a filler material having less than 0.3% by weight of water relative to the filler material weight. The % water (equal to residual total moisture content) is determined as described herein.

As used herein, the term "polymer" generally includes homopolymers and co-polymers such as, for example, block, graft, random and alternating copolymers, as well as blends and modifications thereof. The polymer can be an amorphous polymer, a crystalline polymer, or a semi-crystalline polymer, i.e. a polymer comprising crystalline and amorphous fractions. The degree of crystallinity is specified in percent and can be determined by differential scanning calorimetry (DSC). An amorphous polymer may be characterized by its glass transition temperature and a crystalline polymer may be characterized by its melting point. A semi-crystalline polymer may be characterized by its glass transition temperature and/or its melting point.

For the purposes of the present invention, "polyethylene" is understood to relate to a polymer, which is derived from at least 50 mol-%, preferably at least 75 mol-%, more preferably at least 90 mol-% polyethylene monomers, based on the total amount of monomers in the polymer. Likewise, "polypropylene" is understood to designate a polymer, which is derived from at least 50 mol-%, preferably at least 75 mol-%, more preferably at least 90 mol-% polypropylene monomers, based on the total amount of monomers in the polymer; and "polybutylene" is understood to designate a polymer, which is derived from at least 50 mol-%, preferably at least 75 mol-%, more preferably at least 90 mol-% polybutylene monomers, based on the total amount of monomers in the polymer.

The expression "isotactic polymer" refers to a polymer, wherein more than 95%, preferably more than 97% of all substituents are located on the same side of the macromolecular backbone.

The term "melt flow rate" (MFR) as used herein refers to the mass of the polymer, given in g/10 min, which is discharged through a defined die under specified temperature and pressure conditions. For polyethylene polymers, the MFR is commonly measured under a load of 2.16 kg at 190° C., according to EN ISO 1133:2011. For polypropylene polymers, the MFR is commonly measured under a load of 2.16 kg at 230° C., according to EN ISO 1133:2011. The MFR is a measure of the viscosity of the polymer, which is mainly influenced by the molecular weight of the polymer, but also by the degree of branching or the polydispersity.

The expression "polydispersity index" ($M_w/M_n$) as used herein is a measure of the molecular mass distribution and refers to the ratio of the weight-average molar mass and the number-average molar mass of the polymers as determined by gel permeation chromatography (GPC), e.g., according to EN ISO 16014-1:2019.

The term "polymer composition" refers to a composite material comprising at least one additive (e.g., at least one filler) and at least one polymer material which may be used in the production of a polymer product.

The term "polymer masterbatch" (or "masterbatch") relates to a composition with a relatively high filler content, preferably at least or equal to 60 wt.-% (based on the total weight of the composition). A "polymer masterbatch" may be added to an unfilled or lowly filled polymer during processing in order to achieve higher filler contents. Nevertheless, a "polymer composition" (or "composition") as defined earlier having a relative low filler content, preferably below 60 wt.-% (based on the total weight of the composition), and which often also referred to as a "polymer compound" (or "compound"), may also be used directly in the production of a polymer product.

Accordingly, the term "polymer composition" (composition) as used herein comprises both, "polymer masterbatches" and "polymer compounds".

For the purpose of the present invention, the "solids content" of a liquid composition is a measure of the amount of material remaining after all the solvent or water has been evaporated.

A "suspension" or "slurry" in the meaning of the present invention comprises insoluble solids and water, and optionally further additives, and usually contains large amounts of solids and, thus, is more viscous and can be of higher density than the liquid from which it is formed.

A "treatment layer" in the meaning of the present invention refers to a layer, preferably a monolayer of a surface treatment agent on the surface of the at least one calcium carbonate-comprising filler material.

As used herein, "hydrostatic pressure" is a measure of the breathable film's resistance to liquid penetration, this means its barrier properties. The barrier properties of a breathable film were measured by using the hydrostatic pressure test which measures the resistance of the film sample to the penetration of water under hydrostatic pressure. The hydrostatic pressure test has been carried out according to a procedure which is equivalent to AATCC Test Method 127-2013, WSP 80.6 and ISO 811:2018. A film sample (test area=10 $cm^2$) was mounted to form a cover on the test head reservoir. This film sample was subjected to a standardized water pressure, increased at a constant rate until leakage appears on the outer surface of the film, or water burst occurred as a result of film failure (pressure rate gradient=100 mbar/min.). Water pressure was measured as the hydrostatic head height reached at the first sign of leakage in three separate areas of the film sample or when burst occurs. The head height results were recorded in centimetres or millibars of water pressure on the specimen. A higher value indicated greater resistance to water penetration. The TEXTEST FX-3000, Hydrostatic Head Tester (Textest AG, Switzerland), was used for the hydrostatic pressure measurements.

The "machinability" is considered to be a measure of the stability of the process for producing the inventive breathable film. The machinability is reflected by a favorable or negligible pressure increase in the extruder determined as outlined herein.

Where the term "comprising" is used in the present description and claims, it does not exclude other non-specified elements of major or minor functional importance. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" even though such a limited understanding is always included by the terms "obtained" or "defined" as a preferred embodiment.

When in the following reference is made to embodiments or technical details of the inventive breathable film, it is to be understood that these embodiments or technical details also refer to the inventive process, the inventive uses and the inventive article.

The at Least One Thermoplastic Polymer

The inventive breathable film, the inventive process, the inventive uses and the inventive article make use of at least one thermoplastic polymer. It is appreciated that the at least one thermoplastic polymer is not restricted to a specific material as long as the polymer is suitable for the preparation of a breathable film. The skilled person will select the thermoplastic polymer in accordance with the desired properties of the breathable film such as temperature resistance or elastic recovery.

It is appreciated that the expression "at least one" thermoplastic polymer means that the thermoplastic polymer comprises, preferably consists of, one or more kinds of thermoplastic polymer(s).

Accordingly, it should be noted that the at least one thermoplastic polymer may be one kind of thermoplastic polymer. Alternatively, the at least one thermoplastic polymer may be a mixture of two or more kinds of thermoplastic polymers. For example, the at least one thermoplastic polymer may be a mixture of two or three kinds of thermoplastic polymers, like two kinds of thermoplastic polymers.

In one embodiment of the present invention, the at least one thermoplastic polymer comprises, preferably consists of, two kinds of thermoplastic polymers. Alternatively, the at least one thermoplastic polymer comprises, preferably consists of, one kind of thermoplastic polymer.

According to a preferred embodiment, the at least one thermoplastic polymer is a polyolefin. Polyolefin polymers that may be used are preferably selected from the group consisting of polypropylene, polyethylene, polybutylene, and mixtures thereof.

According to a particularly preferred embodiment, the at least one thermoplastic polymer is a polyethylene, preferably selected from the group consisting of high density polyethylene (HDPE), linear low density polyethylene (LLDPE), low density polyethylene (LDPE), ultra-low density polyethylene (ULDPE), very low density polyethylene (VLDPE), and mixtures thereof.

A polyethylene having a density ranging from 0.936 $g/cm^3$ to about 0.965 $g/cm^3$ is typically called "high density polyethylenes (HDPE)". A polyethylene having a density ranging from 0.910 $g/cm^3$ to about 0.940 $g/cm^3$ is typically called "low density polyethylenes (LDPE)".

The term "linear low density polyethylene (LLDPE)" refers to a substantially linear polymer (polyethylene), with significant numbers of short branches, commonly made by copolymerization of ethylene with longer-chain olefins. Linear low-density polyethylene differs structurally from low-density polyethylene (LDPE) in the absence of long chain branching. The linearity of LLDPE results from the different manufacturing processes of LLDPE. In general, LLDPE is produced at lower temperatures and pressures by copolymerization of ethylene and higher alpha-olefins such as 1-butene, 1-hexene, or 1-octene. LLDPE has typically a density in the range from 0.911 $g/cm^3$ to 0.940 $g/cm^3$, and preferably in the range from 0.912 $g/cm^3$ to 0.928 $g/cm^3$ for breathable film applications.

"Very low density linear low density polyethylenes" (VLDPE) is a substantially linear polymer with high levels of short-chain branches, commonly made by copolymerization of ethylene with short-chain alpha-olefins such as 1-butene, 1-hexene or 1-octene. VLDPE has typically a density in the range from 0.900 to 0.914 $g/cm^3$.

"Ultra-low density linear low density polyethylenes" (ULDPE) is a substantially linear polymer with high levels of short-chain branches, commonly made by copolymerization of ethylene with short-chain alpha-olefins such as 1-butene, 1-hexene or 1-octene. ULDPE has typically a density in the range from 0.860 to 0.899 g/cm$^3$.

According to one embodiment, the thermoplastic polymer comprises a linear low density polyethylene (LLDPE), preferably a LLDPE having a density in the range from 0.912 g/cm$^3$ to 0.928 g/cm$^3$. The inventors found that LLDPE polymers having a density in said range may show very good barrier and processability properties, especially in combination with the surface-treated filler material according to the present invention. If the thermoplastic polymer comprises a linear low density polyethylene (LLDPE), the at least one thermoplastic polymer comprises 80 to 98 wt.-% LLDPE, more preferably 86 to 94 wt.-% LLDPE, and most preferably about 90 wt.-% LLDPE, based on the total amount of thermoplastic polymer.

According to one embodiment, the at least one thermoplastic polymer comprises 2 to 20 wt.-% LDPE, more preferably 6 to 14 wt.-% LDPE, and most preferably about 10 wt.-% LDPE, based on the total amount of thermoplastic polymer.

For example, the at least one thermoplastic polymer comprises, preferably consists of, 80 to 98 wt.-% LLDPE, more preferably 86 to 94 wt.-% LLDPE, and most preferably about 90 wt.-% LLDPE, based on the total amount of thermoplastic polymer and 2 to 20 wt.-% LDPE, more preferably 6 to 14 wt.-% LDPE, and most preferably about 10 wt.-% LDPE, based on the total amount of thermoplastic polymer. It is appreciated that the sum of the amounts of the LLDPE and of the LDPE is preferably 100 wt.-%, based on the total amount of thermoplastic polymer.

In an alternative embodiment, the at least one thermoplastic polymer comprises, preferably consists of, a LLDPE and LDPE in a specific weight ratio. For example, the at least one thermoplastic polymer comprises, preferably consists of, a LLDPE and LDPE in a weight ratio [LLDPE: LDPE] from 40:10 to 45:5, and most preferably of about 45:5, wherein the density of the LLDPE is from 0.912 g/cm$^3$ to 0.928 g/cm$^3$ and the density of the LDPE is from 0.910 g/cm$^3$ to about 0.940 g/cm$^3$.

According to another embodiment, the thermoplastic polymer comprises a polypropylene (PP), preferably a PP having a density in the range from 0.890 g/cm$^3$ to 0.910 g/cm$^3$. If the thermoplastic polymer comprises a polypropylene (PP), the at least one thermoplastic polymer comprises 10 to 30 wt.-% PP, more preferably 15 to 25 wt.-% PP, and most preferably about 20 wt.-% PP, based on the total amount of thermoplastic polymer.

Additionally or alternatively, the thermoplastic polymer comprises a polyethylene (PE), preferably a PE having a density in the range from 0.912 g/cm$^3$ to 0.928 g/cm$^3$. For example, the PE is a bimodal linear low density polyethylene (LLDPE). If the thermoplastic polymer comprises a polyethylene (PE), the at least one thermoplastic polymer comprises 70 to 90 wt.-% PE, more preferably 75 to 85 wt.-% PE, and most preferably about 80 wt.-% PE, based on the total amount of thermoplastic polymer.

For example, the at least one thermoplastic polymer comprises, preferably consists of, 10 to 30 wt.-% PP, more preferably 15 to 25 wt.-% PP, and most preferably about 20 wt.-% PP, based on the total amount of thermoplastic polymer, and 70 to 90 wt.-% PE, more preferably 75 to 85 wt.-% PE, and most preferably about 80 wt.-% PE, based on the total amount of thermoplastic polymer. It is appreciated that the sum of the amounts of the PP and of the PE is preferably 100 wt.-%, based on the total amount of thermoplastic polymer.

Alternatively, the at least one thermoplastic polymer comprises, preferably consists of, a polypropylene (PP) having a density in the range from 0.890 g/cm$^3$ to 0.910 g/cm$^3$.

In another embodiment the at least one thermoplastic polymer comprises, preferably consists of, a polyethylene (PE) and polypropylene (PP) in a specific weight ratio. For example, the at least one thermoplastic polymer comprises, preferably consists of, a polyethylene (PE) and polypropylene (PP) in a weight ratio [PE:PP] from 40:10 to 45:5, and most preferably of about 40:10, wherein the density of the polyethylene (PE) is from 0.912 g/cm$^3$ to 0.928 g/cm$^3$ and the density of the polypropylene (PP) is from 0.890 g/cm$^3$ to 0.910 g/cm$^3$.

According to one embodiment of the present invention, the melt flow rate (MFR) determined according to ISO 1133:2011 (190° C., 2.16 kg) of the at least one thermoplastic polymer is preferably from 0.01 to 20, and more preferably from 0.1 to 10 g/10 min. Alternatively, the melt flow rate (MFR) determined according to ISO 1133:2011 (230° C., 2.16 kg) of the at least one thermoplastic polymer is preferably from 0.01 to 20, and more preferably from 0.1 to 10 g/10 min. For example, if the thermoplastic polymer is a polyethylene, it is preferred that the melt flow rate (MFR) determined according to ISO 1133:2011 (190° C., 2.16 kg) of the at least one thermoplastic polymer is preferably from 0.01 to 20, and more preferably from 0.1 to 10 g/10 min. If the thermoplastic polymer is a polypropylene, it is preferred that the melt flow rate (MFR) determined according to ISO 1133:2011 (230° C., 2.16 kg) of the at least one thermoplastic polymer is preferably from 0.01 to 20, and more preferably from 0.1 to 10 g/10 min.

The breathable film can comprise the at least one thermoplastic polymer in an amount of at least 15 wt.-%, based on the total weight of the breathable film, preferably of at least 20 wt.-%, more preferably of at least 30 wt.-%, and most preferably at least 40 wt.-%, for example, about 50 wt.-%. According to one embodiment, the breathable film comprises the at least one thermoplastic polymer in an amount from 15 to 70 wt.-%, preferably from 20 to 70 wt.-%, more preferably from 30 to 65 wt.-%, and most preferably from 40 to 60 wt.-%, based on the total weight of the breathable film.

Surface-Treated Filler Material

The inventive breathable film, the inventive process, the inventive uses and the inventive article make use of a surface-treated filler material, wherein the surface-treated filler material comprises at least one calcium carbonate-comprising filler material having several essential features, which will be described in more detail in the following.

The at least one calcium carbonate-comprising filler material in the meaning of the present invention refers to a filler material preferably selected from natural ground calcium carbonate (GCC), precipitated calcium carbonate (PCC), surface-reacted calcium carbonate (SRCC), or mixtures thereof. According to a preferred embodiment, the at least one calcium carbonate-comprising filler material is a natural ground calcium carbonate (GCC), more preferably the ground calcium carbonate-carbonate comprising filler is a wet ground natural ground calcium carbonate.

GCC is understood to be a naturally occurring form of calcium carbonate, mined from sedimentary rocks such as limestone or chalk, or from metamorphic marble rocks and processed through a treatment such as grinding, screening and/or fractionizing in wet form, for example by a cyclone or classifier. In one embodiment of the present invention, the GCC is selected from the group comprising marble, chalk, dolomite, limestone and mixtures thereof.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried. PCCs are described, for example, in EP2447213 A1, EP2524898 A1, EP2371766 A1, EP2840065 A1, or WO2013/142473 A1.

A "surface-reacted calcium carbonate" according to the present invention is a reaction product of ground natural calcium carbonate (GNCC) or precipitated calcium carbonate (PCC) treated with carbon dioxide and one or more $H_3O^+$ ion donors, wherein the carbon dioxide is formed in situ by the $H_3O^+$ ion donors treatment and/or is supplied from an external source. A $H_3O^+$ ion donor in the context of the present invention is a Brønsted acid and/or an acid salt. Surface-reacted calcium carbonates are described, for example, in US2012/0031576 A1, WO2009/074492 A1, EP2264109 A1, EP2070991 A1, or EP2264108 A1.

In one preferred embodiment, the at least one calcium carbonate-comprising filler material is a ground natural calcium carbonate, preferably marble, more preferably a wet ground marble.

It is appreciated that the amount of calcium carbonate in the at least one calcium carbonate-comprising filler material is at least 50 wt.-%, preferably at least 80 wt.-%, e.g. at least 95 wt.-%, more preferably between 97 and 100 wt.-% and most preferably between 98.5 and 99.95 wt.-%, based on the total dry weight of the at least one calcium carbonate-comprising filler material.

The at least one calcium carbonate-comprising filler material is preferably in the form of a particulate material, and has a specific particle size distribution. It is one specific requirement of the present invention that the at least one calcium carbonate-comprising filler material has a weight median particle size $d_{50}$ value in the range from 0.1 to 7 μm. For example, the at least one calcium carbonate-comprising filler material has a weight median particle size $d_{50}$ from 0.25 μm to 5 μm, preferably from 0.5 μm to 4 μm and most preferably from 0.6 μm to 1 μm.

A further requirement of the present invention is that the at least one calcium carbonate-comprising filler material has a top cut ($d_{98}$) of ≤15 μm. For example, the at least one calcium carbonate-comprising filler material has a top cut ($d_{98}$) of ≤12.5 μm, preferably of ≤10 μm, more preferably of ≤7.5 μm and most preferably of ≤3 μm.

The weight median particle size $d_{50}$ value and the top cut ($d_{98}$) of the at least one calcium carbonate-comprising filler material may fulfil a specific ratio. For example, the at least one calcium carbonate-comprising filler material may have a ratio of weight median particle size $d_{50}$ value and the top cut ($d_{98}$) [$d_{50}/d_{98}$] of from 0.1 to 0.4, preferably from 0.1 to 0.3 and most preferably from 0.15 to 0.25.

It is a further requirement that the at least one calcium carbonate-comprising filler material has a fineness (<0.5 μm) such that at least 15 wt.-%, preferably at least 20 wt.-%, even more preferably at least 30 wt.-% and most preferably at least 35 wt.-% of all particles have a particle size of <0.5 μm.

The at least one calcium carbonate-comprising filler material may have a fineness (<1 μm) such that at least 65 wt.-%, preferably at least 70 wt.-%, even more preferably at least 75 wt.-% and most preferably at least 80 wt.-% of all particles have a particle size of ≤1 μm.

In one embodiment, the at least one calcium carbonate-comprising filler material has a fineness (<0.5 μm) such that at least 10 wt.-%, preferably from 10 to 70 wt.-%, even more preferably from 10 to 60 wt.-% and most preferably from 10 to 50 wt.-% of all particles have a particle size of <0.5 μm. For example, from 10 to 15 wt.-% of all particles have a particle size of <0.5 μm. Alternatively, from 30 to 45 wt.-% of all particles have a particle size of <0.5 μm.

It is specifically advantageous if the at least one calcium carbonate-comprising filler material comprises a high amount of fine particles. Preferably, the at least one calcium carbonate-comprising filler material has a fineness such that at least 80 wt.-% of all particles have a particle size of ≤1 μm and from 30 to 45 wt.-% of all particles have a particle size of <0.5 μm.

In one embodiment, the at least one calcium carbonate-comprising filler material has i) a weight median particle size $d_{50}$ from 0.25 μm to 5 μm, preferably from 0.5 μm to 4 μm and most preferably from 0.6 μm to 1 μm, and ii) a top cut ($d_{98}$) of ≤12.5 μm, preferably of ≤10 μm, more preferably of ≤7.5 μm and most preferably of ≤3 μm, and iii) a fineness (<0.5 μm) such that at least 15 wt.-%, preferably at least 20 wt.-%, even more preferably at least 25 wt.-% and most preferably at least 30 wt.-% of all particles have a particle size of <0.5 μm.

Most preferably, the at least one calcium carbonate-comprising filler material has i) a weight median particle size $d_{50}$ from 0.6 μm to 1 μm, and ii) a top cut ($d_{98}$) of ≤10 μm, preferably of ≤7.5 μm and most preferably of ≤3 μm, and iii) a fineness (<0.5 μm) such that at least 20 wt.-%, preferably at least 25 wt.-% and most preferably at least 30 wt.-% of all particles have a particle size of <0.5 μm.

The present inventors realized that thin breathable films can only be produced if the particle size of the at least one calcium carbonate-comprising filler material is sufficiently low. It is not possible to produce thin breathable films having a thickness which is lower than the particle size of the at least one calcium carbonate-comprising filler material. Thus, it is preferred that the top cut $d_{98}$ does not exceed the film thickness of the breathable film. Furthermore, the present inventors realized that larger particles tend to induce larger voids, or even holes, which deteriorate the mechanical properties and liquid barrier properties of the films. Consequently, the at least one calcium carbonate-comprising filler material must have a weight median particle size $d_{50}$ and a fineness (<0.5 μm) as defined herein.

In another preferred embodiment, the at least one calcium carbonate-comprising filler material has a BET specific surface area of from 0.5 and 150 $m^2/g$, as measured using nitrogen and the BET method according to ISO 9277:2010. For example, the at least one calcium carbonate-comprising filler material has a specific surface area (BET) of from 1 to 50 $m^2/g$, more preferably of from 2 to 35 $m^2/g$ and most preferably of from 4 to 15 $m^2/g$, as measured using nitrogen and the BET method according to ISO 9277:2010.

In one embodiment of the present invention, the at least one calcium carbonate-comprising filler material is preferably a ground natural calcium carbonate (preferably marble) having a median particle size diameter $d_{50}$ value from 0.1 μm to 7 μm, preferably from 0.25 μm to 5 μm, more preferably from 0.5 μm to 4 μm and most preferably from 0.6 μm to 1 μm. In this case, the at least one calcium carbonate-comprising filler material may exhibit a BET specific surface area of from 0.5 to 150 $m^2/g$, preferably of from 0.5 to 50 $m^2/g$, more preferably of from 0.5 to 35 $m^2/g$ and most preferably of from 0.5 to 15 $m^2/g$, measured using nitrogen and the BET method according to ISO 9277:2010.

In a preferred embodiment the ground natural calcium carbonate-comprising filler is a wet ground calcium carbonate-comprising filler. However, dry ground calcium carbonate-comprising fillers may also be used.

The wet grinding step may be performed under conditions such that autogenous grinding takes place and/or by horizontal ball milling, and/or other such processes known to the skilled man. The processed ground calcium carbonate-comprising filler material thus obtained may be washed and dewatered by well-known processes, e.g. by flocculation, filtration or forced evaporation prior to drying. The subsequent step of drying may be carried out in a single step such as spray drying, or in at least two steps, e.g. by applying a first heating step to the wet ground calcium carbonate-comprising filler material in order to reduce the associated moisture content to a level which is not greater than about 0.5 wt.-%, based on the total dry weight of the at least one wet ground calcium carbonate-comprising filler material. The residual total moisture content of the filler can be measured by the Karl Fischer Coulometric titration method, desorbing the moisture in an oven at 195° C. and passing it continuously into the KF Coulometer (Mettler Toledo Coulometric KF Titrator C30, combined with Mettler oven DO 0337) using dry $N_2$ at 100 ml/min for 10 min. The residual total moisture content can be determined with a calibration curve and also a blind of 10 min gas flow without a sample can be taken into account. The residual total moisture content may be further reduced by applying a second heating step to the at least one wet ground calcium carbonate-comprising filler material. In case said drying is carried out by more than one drying steps, the first step may be carried out by heating in a hot current of air, while the second and further drying steps are preferably carried out by an indirect heating in which the atmosphere in the corresponding vessel comprises a surface treatment agent. It is also common that the at least one wet ground calcium carbonate-comprising filler material is subjected to a beneficiation step (such as a flotation, bleaching or magnetic separation step) to remove impurities.

In another preferred embodiment, the at least one calcium carbonate-comprising filler material is a material being ground in a horizontal ball mill, and subsequently dried by using the well-known process of spray drying.

According to the present invention, the at least one calcium carbonate-comprising filler material has a residual moisture content of ≤1 wt.-%, based on the total dry weight of the at least one calcium carbonate-comprising filler material. Depending on the at least one calcium carbonate-comprising filler material, the at least one calcium carbonate-comprising filler material has a residual total moisture content of from 0.01 to 1 wt.-%, preferably from 0.01 to 0.2 wt.-%, more preferably from 0.02 to 0.15 wt.-% and most preferably from 0.04 to 0.15 wt.-%, based on the total dry weight of the at least one calcium carbonate-comprising filler material.

For example, in case a ground (especially wet ground) and spray dried marble is used as the at least one calcium carbonate-comprising filler material, the residual total moisture content of the at least one calcium carbonate-comprising filler material is preferably of from 0.01 to 0.1 wt.-%, more preferably from 0.02 to 0.08 wt.-% and most preferably from 0.04 to 0.07 wt.-% based on the total dry weight of the at least one calcium carbonate-comprising filler material. If a PCC is used as the at least one calcium carbonate-comprising filler material, the residual total moisture content of the at least one calcium carbonate-comprising filler material is preferably of from 0.01 to 0.2 wt.-%, more preferably from 0.05 to 0.17 wt.-% and most preferably from 0.05 to 0.10 wt.-%, based on the total dry weight of the at least one calcium carbonate-comprising filler material.

Surface-Treatment Layer

According to the present invention, the surface-treated filler material further comprises a treatment layer on the surface of the at least one calcium carbonate-comprising filler material. The treatment layer comprises at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

It is appreciated that the expression "at least one" mono-substituted succinic anhydride means that one or more kinds of mono-substituted succinic anhydride may be provided in the process of the present invention.

Accordingly, it should be noted that the at least one mono-substituted succinic anhydride may be one kind of mono-substituted succinic anhydride. Alternatively, the at least one mono-substituted succinic anhydride may be a mixture of two or more kinds of mono-substituted succinic anhydride. For example, the at least one mono-substituted succinic anhydride may be a mixture of two or three kinds of mono-substituted succinic anhydride, like two kinds of mono-substituted succinic anhydride.

In one embodiment of the present invention, the at least one mono-substituted succinic anhydride is one kind of mono-substituted succinic anhydride.

It is appreciated that the at least one mono-substituted succinic anhydride represents a surface treatment agent and consists of succinic anhydride mono-substituted with a group selected from any linear, branched, aliphatic or cyclic group having a total amount of carbon atoms from C2 to C30 in the substituent.

In one embodiment of the present invention, the at least one mono-substituted succinic anhydride consists of succinic anhydride mono-substituted with a group selected from a linear, branched, aliphatic or cyclic group having a total amount of carbon atoms from C3 to C20 in the substituent. For example, the at least one mono-substituted succinic anhydride consists of succinic anhydride mono-substituted with a group selected from a linear, branched, aliphatic or cyclic group having a total amount of carbon atoms from C4 to C18 in the substituent.

In one embodiment of the present invention, the at least one mono-substituted succinic anhydride consists of succinic anhydride mono-substituted with one group being a linear and aliphatic group having a total amount of carbon atoms from C2 to C30, preferably from C3 to C20 and most preferably from C4 to C18 in the substituent. Additionally or alternatively, the at least one mono-substituted succinic anhydride consists of succinic anhydride mono-substituted with one group being a branched and aliphatic group having a total amount of carbon atoms from C2 to C30, preferably from C3 to C20 and most preferably from C4 to C18 in the substituent.

Thus, it is preferred that the at least one mono-substituted succinic anhydride consists of succinic anhydride mono-substituted with one group being a linear or branched, alkyl group having a total amount of carbon atoms from C2 to C30, preferably from C3 to C20 and most preferably from C4 to C18 in the substituent.

For example, the at least one mono-substituted succinic anhydride consists of succinic anhydride mono-substituted with one group being a linear alkyl group having a total amount of carbon atoms from C2 to C30, preferably from C3 to C20 and most preferably from C4 to C18 in the substituent. Additionally or alternatively, the at least one mono-substituted succinic anhydride consists of succinic anhydride mono-substituted with one group being a branched alkyl group having a total amount of carbon atoms from C2 to C30, preferably from C3 to C20 and most preferably from C4 to C18 in the substituent.

The term "alkyl" in the meaning of the present invention refers to a linear or branched, saturated organic compound composed of carbon and hydrogen. In other words, "alkyl mono-substituted succinic anhydrides" are composed of linear or branched, saturated hydrocarbon chains containing a pendant succinic anhydride group.

In one embodiment of the present invention, the at least one mono-substituted succinic anhydride is at least one linear or branched alkyl mono-substituted succinic anhydride. For example, the at least one alkyl mono-substituted succinic anhydride is selected from the group comprising ethylsuccinic anhydride, propylsuccinic anhydride, butylsuccinic anhydride, triisobutyl succinic anhydride, pentylsuccinic anhydride, hexylsuccinic anhydride, heptylsuccinic anhydride, octylsuccinic anhydride, nonylsuccinic anhydride, decyl succinic anhydride, dodecyl succinic anhydride, hexadecanyl succinic anhydride, octadecanyl succinic anhydride, and mixtures thereof.

Accordingly, it is appreciated that e.g. the term "butylsuccinic anhydride" comprises linear and branched butylsuccinic anhydride(s). One specific example of linear butylsuccinic anhydride(s) is n-butylsuccinic anhydride. Specific examples of branched butylsuccinic anhydride(s) are iso-butylsuccinic anhydride, sec-butylsuccinic anhydride and/or tert-butylsuccinic anhydride.

Furthermore, it is appreciated that e.g. the term "hexadecanyl succinic anhydride" comprises linear and branched hexadecanyl succinic anhydride(s). One specific example of linear hexadecanyl succinic anhydride(s) is n-hexadecanyl succinic anhydride. Specific examples of branched hexadecanyl succinic anhydride(s) are 14-methylpentadecanyl succinic anhydride, 13-methylpentadecanyl succinic anhydride, 12-methylpentadecanyl succinic anhydride, 11-methylpentadecanyl succinic anhydride, 10-methylpentadecanyl succinic anhydride, 9-methylpentadecanyl succinic anhydride, 8-methylpentadecanyl succinic anhydride, 7-methylpentadecanyl succinic anhydride, 6-methylpentadecanyl succinic anhydride, 5-methylpentadecanyl succinic anhydride, 4-methylpentadecanyl succinic anhydride, 3-methylpentadecanyl succinic anhydride, 2-methylpentadecanyl succinic anhydride, 1-methylpentadecanyl succinic anhydride, 13-ethylbutadecanyl succinic anhydride, 12-ethylbutadecanyl succinic anhydride, 11-ethylbutadecanyl succinic anhydride, 10-ethylbutadecanyl succinic anhydride, 9-ethylbutadecanyl succinic anhydride, 8-ethylbutadecanyl succinic anhydride, 7-ethylbutadecanyl succinic anhydride, 6-ethylbutadecanyl succinic anhydride, 5-ethylbutadecanyl succinic anhydride, 4-ethylbutadecanyl succinic anhydride, 3-ethylbutadecanyl succinic anhydride, 2-ethylbutadecanyl succinic anhydride, 1-ethylbutadecanyl succinic anhydride, 2-butyldodecanyl succinic anhydride, 1-hexyldecanyl succinic anhydride, 1-hexyl-2-decanyl succinic anhydride, 2-hexyldecanyl succinic anhydride, 6,12-dimethylbutadecanyl succinic anhydride, 2,2-diethyldodecanyl succinic anhydride, 4,8,12-trimethyltridecanyl succinic anhydride, 2,2,4,6,8-pentamethylundecanyl succinic anhydride, 2-ethyl-4-methyl-2-(2-methylpentyl)-heptyl succinic anhydride and/or 2-ethyl-4,6-dimethyl-2-propylnonyl succinic anhydride.

Furthermore, it is appreciated that e.g. the term "octadecanyl succinic anhydride" comprises linear and branched octadecanyl succinic anhydride(s). One specific example of linear octadecanyl succinic anhydride(s) is n-octadecanyl succinic anhydride. Specific examples of branched hexadecanyl succinic anhydride(s) are 16-methylheptadecanyl succinic anhydride, 15-methylheptadecanyl succinic anhydride, 14-methylheptadecanyl succinic anhydride, 13-methylheptadecanyl succinic anhydride, 12-methylheptadecanyl succinic anhydride, 11-methylheptadecanyl succinic anhydride, 10-methylheptadecanyl succinic anhydride, 9-methylheptadecanyl succinic anhydride, 8-methylheptadecanyl succinic anhydride, 7-methylheptadecanyl succinic anhydride, 6-methylheptadecanyl succinic anhydride, 5-methylheptadecanyl succinic anhydride, 4-methylheptadecanyl succinic anhydride, 3-methylheptadecanyl succinic anhydride, 2-methylheptadecanyl succinic anhydride, 1-methylheptadecanyl succinic anhydride, 14-ethylhexadecanyl succinic anhydride, 13-ethylhexadecanyl succinic anhydride, 12-ethylhexadecanyl succinic anhydride, 11-ethylhexadecanyl succinic anhydride, 10-ethylhexadecanyl succinic anhydride, 9-ethylhexadecanyl succinic anhydride, 8-ethylhexadecanyl succinic anhydride, 7-ethylhexadecanyl succinic anhydride, 6-ethylhexadecanyl succinic anhydride, 5-ethylhexadecanyl succinic anhydride, 4-ethylhexadecanyl succinic anhydride, 3-ethylhexadecanyl succinic anhydride, 2-ethylhexadecanyl succinic anhydride, 1-ethylhexadecanyl succinic anhydride, 2-hexyldodecanyl succinic anhydride, 2-heptylundecanyl succinic anhydride, iso-octadecanyl succinic anhydride and/or 1-octyl-2-decanyl succinic anhydride.

In one embodiment of the present invention, the at least one alkyl mono-substituted succinic anhydride is selected from the group comprising butylsuccinic anhydride, hexylsuccinic anhydride, heptylsuccinic anhydride, octylsuccinic anhydride, hexadecanyl succinic anhydride, octadecanyl succinic anhydride, and mixtures thereof.

In one embodiment of the present invention, the at least one mono-substituted succinic anhydride is one kind of alkyl mono-substituted succinic anhydride. For example, the one alkyl mono-substituted succinic anhydride is butylsuccinic anhydride. Alternatively, the one alkyl mono-substituted succinic anhydride is hexylsuccinic anhydride. Alternatively, the one alkyl mono-substituted succinic anhydride is heptylsuccinic anhydride or octylsuccinic anhydride. Alternatively, the one alkyl mono-substituted succinic anhydride is hexadecanyl succinic anhydride. For example, the one alkyl mono-substituted succinic anhydride is linear hexadecanyl succinic anhydride such as n-hexadecanyl succinic anhydride or branched hexadecanyl succinic anhydride such as 1-hexyl-2-decanyl succinic anhydride. Alternatively, the one alkyl mono-substituted succinic anhydride is octadecanyl succinic anhydride. For example, the one alkyl mono-substituted succinic anhydride is linear octadecanyl succinic anhydride such as n-octadecanyl succinic anhydride or branched octadecanyl succinic anhydride such as iso-octadecanyl succinic anhydride or 1-octyl-2-decanyl succinic anhydride.

In one embodiment of the present invention, the one alkyl mono-substituted succinic anhydride is butylsuccinic anhydride such as n-butylsuccinic anhydride.

In one embodiment of the present invention, the at least one mono-substituted succinic anhydride is a mixture of two or more kinds of alkyl mono-substituted succinic anhydrides. For example, the at least one mono-substituted succinic anhydride is a mixture of two or three kinds of alkyl mono-substituted succinic anhydrides.

In a preferred embodiment of the present invention, the at least one mono-substituted succinic anhydride comprises, preferably consists of, succinic anhydride mono-substituted with one group being a linear or branched alkenyl group having a total amount of carbon atoms from C2 to C30, preferably from C3 to C20 and most preferably from C4 to C18 in the substituent.

The term "alkenyl" in the meaning of the present invention refers to a linear or branched, unsaturated organic compound composed of carbon and hydrogen. Said organic compound further contains at least one double bond in the substituent, preferably one double bond. In other words, "alkenyl mono-substituted succinic anhydrides" are composed of linear or branched, unsaturated hydrocarbon chains containing a pendant succinic anhydride group. It is appreciated that the term "alkenyl" in the meaning of the present invention includes the cis and trans isomers.

In one embodiment of the present invention, the at least one mono-substituted succinic anhydride is at least one linear or branched alkenyl mono-substituted succinic anhydride. For example, the at least one alkenyl mono-substituted succinic anhydride is selected from the group comprising ethenylsuccinic anhydride, propenylsuccinic anhydride, butenylsuccinic anhydride, triisobutenyl succinic anhydride, pentenylsuccinic anhydride, hexenylsuccinic anhydride, heptenylsuccinic anhydride, octenylsuccinic anhydride, nonenylsuccinic anhydride, decenyl succinic anhydride, dodecenyl succinic anhydride, hexadecenyl succinic anhydride, octadecenyl succinic anhydride, and mixtures thereof.

Accordingly, it is appreciated that e.g. the term "hexadecenyl succinic anhydride" comprises linear and branched hexadecenyl succinic anhydride(s). One specific example of linear hexadecenyl succinic anhydride(s) is n-hexadecenyl succinic anhydride such as 14-hexadecenyl succinic anhydride, 13-hexadecenyl succinic anhydride, 12-hexadecenyl succinic anhydride, 11-hexadecenyl succinic anhydride, 10-hexadecenyl succinic anhydride, 9-hexadecenyl succinic anhydride, 8-hexadecenyl succinic anhydride, 7-hexadecenyl succinic anhydride, 6-hexadecenyl succinic anhydride, 5-hexadecenyl succinic anhydride, 4-hexadecenyl succinic anhydride, 3-hexadecenyl succinic anhydride and/or 2-hexadecenyl succinic anhydride. Specific examples of branched hexadecenyl succinic anhydride(s) are 14-methyl-9-pentadecenyl succinic anhydride, 14-methyl-2-pentadecenyl succinic anhydride, 1-hexyl-2-decenyl succinic anhydride and/or iso-hexadecenyl succinic anhydride.

Furthermore, it is appreciated that e.g. the term "octadecenyl succinic anhydride" comprises linear and branched octadecenyl succinic anhydride(s). One specific example of linear octadecenyl succinic anhydride(s) is n-octadecenyl succinic anhydride such as 16-octadecenyl succinic anhydride, 15-octadecenyl succinic anhydride, 14-octadecenyl succinic anhydride, 13-octadecenyl succinic anhydride, 12-octadecenyl succinic anhydride, 11-octadecenyl succinic anhydride, 10-octadecenyl succinic anhydride, 9-octadecenyl succinic anhydride, 8-octadecenyl succinic anhydride, 7-octadecenyl succinic anhydride, 6-octadecenyl succinic anhydride, 5-octadecenyl succinic anhydride, 4-octadecenyl succinic anhydride, 3-octadecenyl succinic anhydride and/or 2-octadecenyl succinic anhydride. Specific examples of branched octadecenyl succinic anhydride(s) are 16-methyl-9-heptadecenyl succinic anhydride, 16-methyl-7-heptadecenyl succinic anhydride, 1-octyl-2-decenyl succinic anhydride and/or iso-octadecenyl succinic anhydride.

In one embodiment of the present invention, the at least one alkenyl mono-substituted succinic anhydride is selected from the group comprising hexenylsuccinic anhydride, octenylsuccinic anhydride, hexadecenyl succinic anhydride, octadecenyl succinic anhydride, and mixtures thereof.

In one embodiment of the present invention, the at least one mono-substituted succinic anhydride is one alkenyl mono-substituted succinic anhydride. For example, the one alkenyl mono-substituted succinic anhydride is hexenylsuccinic anhydride. Alternatively, the one alkenyl mono-substituted succinic anhydride is octenylsuccinic anhydride. Alternatively, the one alkenyl mono-substituted succinic anhydride is hexadecenyl succinic anhydride. For example, the one alkenyl mono-substituted succinic anhydride is linear hexadecenyl succinic anhydride such as n-hexadecenyl succinic anhydride or branched hexadecenyl succinic anhydride such as 1-hexyl-2-decenyl succinic anhydride. Alternatively, the one alkenyl mono-substituted succinic anhydride is octadecenyl succinic anhydride. For example, the one alkyl mono-substituted succinic anhydride is linear octadecenyl succinic anhydride such as n-octadecenyl succinic anhydride or branched octadecenyl succinic anhydride such iso-octadecenyl succinic anhydride, or 1-octyl-2-decenyl succinic anhydride.

In one embodiment of the present invention, the one alkenyl mono-substituted succinic anhydride is linear octadecenyl succinic anhydride such as n-octadecenyl succinic anhydride. In another embodiment of the present invention, the one alkenyl mono-substituted succinic anhydride is linear octenylsuccinic anhydride such as n-octenylsuccinic anhydride.

If the at least one mono-substituted succinic anhydride is one alkenyl mono-substituted succinic anhydride, it is appreciated that the one alkenyl mono-substituted succinic anhydride is present in an amount of ≥95 wt.-% and preferably of ≥96.5 wt.-%, based on the total weight of the at least one mono-substituted succinic anhydride.

In one embodiment of the present invention, the at least one mono-substituted succinic anhydride is a mixture of two or more kinds of alkenyl mono-substituted succinic anhydrides. For example, the at least one mono-substituted succinic anhydride is a mixture of two or three kinds of alkenyl mono-substituted succinic anhydrides.

If the at least one mono-substituted succinic anhydride is a mixture of two or more kinds of alkenyl mono-substituted succinic anhydrides, one alkenyl mono-substituted succinic anhydride is linear or branched octadecenyl succinic anhydride, while each further alkenyl mono-substituted succinic anhydride is selected from ethenylsuccinic anhydride, propenylsuccinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof. For example, the at least one mono-substituted succinic anhydride is a mixture of two or more kinds of alkenyl mono-substituted succinic anhydrides, wherein one alkenyl mono-substituted succinic anhydride is linear octadecenyl succinic anhydride and each further alkenyl mono-substituted succinic anhydride is selected from ethenylsuccinic anhydride, propenylsuccinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof. Alternatively, the at least one mono-substituted succinic anhydride is a mixture of two or more kinds of alkenyl mono-substituted succinic anhydrides, wherein one alkenyl mono-substituted succinic anhydride is branched octadecenyl succinic anhydride and each further alkenyl mono-substituted succinic anhydride is selected from ethenylsuccinic anhydride, propenylsuccinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof.

For example, the at least one mono-substituted succinic anhydride is a mixture of two or more kinds of alkenyl mono-substituted succinic anhydrides comprising one or more hexadecenyl succinic anhydride, like linear or branched hexadecenyl succinic anhydride(s), and one or more octadecenyl succinic anhydride, like linear or branched octadecenyl succinic anhydride(s).

In one embodiment of the present invention, the at least one mono-substituted succinic anhydride is a mixture of two or more kinds of alkenyl mono-substituted succinic anhydrides comprising linear hexadecenyl succinic anhydride(s) and linear octadecenyl succinic anhydride(s). Alternatively, the at least one mono-substituted succinic anhydride is a mixture of two or more kinds of alkenyl mono-substituted succinic anhydrides comprising branched hexadecenyl succinic anhydride(s) and branched octadecenyl succinic anhydride(s). For example, the one or more hexadecenyl succinic anhydride is linear hexadecenyl succinic anhydride like n-hexadecenyl succinic anhydride and/or branched hexadecenyl succinic anhydride like 1-hexyl-2-decenyl succinic anhydride. Additionally or alternatively, the one or more octadecenyl succinic anhydride is linear octadecenyl succinic anhydride like n-octadecenyl succinic anhydride and/or branched octadecenyl succinic anhydride like iso-octadecenyl succinic anhydride and/or 1-octyl-2-decenyl succinic anhydride.

If the at least one mono-substituted succinic anhydride is a mixture of two or more kinds of alkenyl mono-substituted succinic anhydrides, it is appreciated that one alkenyl mono-substituted succinic anhydride is present in an amount of from 20 to 60 wt.-% and preferably of from 30 to 50 wt.-%, based on the total weight of the at least one mono-substituted succinic anhydride provided.

For example, if the at least one mono-substituted succinic anhydride is a mixture of two or more kinds of alkenyl mono-substituted succinic anhydrides comprising one or more hexadecenyl succinic anhydride(s), like linear or branched hexadecenyl succinic anhydride(s), and one or more octadecenyl succinic anhydride(s), like linear or branched hexadecenyl succinic anhydride(s), it is preferred that the one or more octadecenyl succinic anhydride(s) is present in an amount of from 20 to 60 wt.-% and preferably of from 30 to 50 wt.-%, based on the total weight of the at least one mono-substituted succinic anhydride.

It is also appreciated that the at least one mono-substituted succinic anhydride may be a mixture of at least one alkyl mono-substituted succinic anhydrides and at least one alkenyl mono-substituted succinic anhydrides.

If the at least one mono-substituted succinic anhydride is a mixture of at least one alkyl mono-substituted succinic anhydrides and at least one alkenyl mono-substituted succinic anhydrides, it is appreciated that the alkyl substituent of the of at least one alkyl mono-substituted succinic anhydrides and the alkenyl substituent of the of at least one alkenyl mono-substituted succinic anhydrides are preferably the same. For example, the at least one mono-substituted succinic anhydride is a mixture of ethylsuccinic anhydride and ethenylsuccinic anhydride. Alternatively, the at least one mono-substituted succinic anhydride is a mixture of propylsuccinic anhydride and propenylsuccinic anhydride. Alternatively, the at least one mono-substituted succinic anhydride is a mixture of butylsuccinic anhydride and butenylsuccinic anhydride. Alternatively, the at least one mono-substituted succinic anhydride is a mixture of triisobutyl succinic anhydride and triisobutenyl succinic anhydride. Alternatively, the at least one mono-substituted succinic anhydride is a mixture of pentylsuccinic anhydride and pentenylsuccinic anhydride. Alternatively, the at least one mono-substituted succinic anhydride is a mixture of hexylsuccinic anhydride and hexenylsuccinic anhydride. Alternatively, the at least one mono-substituted succinic anhydride is a mixture of heptylsuccinic anhydride and heptenylsuccinic anhydride. Alternatively, the at least one mono-substituted succinic anhydride is a mixture of octylsuccinic anhydride and octenylsuccinic anhydride. Alternatively, the at least one mono-substituted succinic anhydride is a mixture of nonylsuccinic anhydride and nonenylsuccinic anhydride. Alternatively, the at least one mono-substituted succinic anhydride is a mixture of decyl succinic anhydride and decenyl succinic anhydride.

Alternatively, the at least one mono-substituted succinic anhydride is a mixture of dodecyl succinic anhydride and dodecenyl succinic anhydride. Alternatively, the at least one mono-substituted succinic anhydride is a mixture of hexadecanyl succinic anhydride and hexadecenyl succinic anhydride. For example, the at least one mono-substituted succinic anhydride is a mixture of linear hexadecanyl succinic anhydride and linear hexadecenyl succinic anhydride or a mixture of branched hexadecanyl succinic anhydride and branched hexadecenyl succinic anhydride. Alternatively, the at least one mono-substituted succinic anhydride is a mixture of octadecanyl succinic anhydride and octadecenyl succinic anhydride. For example, the at least one mono-substituted succinic anhydride is a mixture of linear octadecanyl succinic anhydride and linear octadecenyl succinic anhydride or a mixture of branched octadecanyl succinic anhydride and branched octadecenyl succinic anhydride.

In one embodiment of the present invention, the at least one mono-substituted succinic anhydride is a mixture of nonylsuccinic anhydride and nonenylsuccinic anhydride.

If the at least one mono-substituted succinic anhydride is a mixture of at least one alkyl mono-substituted succinic anhydrides and at least one alkenyl mono-substituted succinic anhydrides, the weight ratio between the at least one alkyl mono-substituted succinic anhydride and the at least one alkenyl mono-substituted succinic anhydride is between 90:10 and 10:90 (wt.-%/wt.-%). For example, the weight ratio between the at least one alkyl mono-substituted succinic anhydride and the at least one alkenyl mono-substituted succinic anhydride is between 70:30 and 30:70 (wt.-%/wt.-%) or between 60:40 and 40:60.

It is appreciated that the expression "at least one" mono-substituted succinic acid means that one or more kinds of mono-substituted succinic acid may be provided in the process of the present invention.

Accordingly, it should be noted that the at least one mono-substituted succinic acid may be one kind of mono-substituted succinic acid. Alternatively, the at least one mono-substituted succinic acid may be a mixture of two or more kinds of mono-substituted succinic acid. For example, the at least one mono-substituted succinic acid may be a mixture of two or three kinds of mono-substituted succinic acid, like two kinds of mono-substituted succinic acid.

In one embodiment of the present invention, the at least one mono-substituted succinic acid is one kind of mono-substituted succinic acid.

It is appreciated that the at least one mono-substituted succinic acid represents a surface treatment agent and consists of succinic acid mono-substituted with a group selected from any linear, branched, aliphatic or cyclic group having a total amount of carbon atoms from C2 to C30 in the substituent.

In one embodiment of the present invention, the at least one mono-substituted succinic acid consists of succinic acid mono-substituted with a group selected from a linear, branched, aliphatic or cyclic group having a total amount of carbon atoms from C3 to C20 in the substituent. For example, the at least one mono-substituted succinic acid consists of succinic acid mono-substituted with a group selected from a linear, branched, aliphatic or cyclic group having a total amount of carbon atoms from C4 to C18 in the substituent.

It is appreciated that the at least one mono-substituted succinic anhydride and the at least one mono-substituted succinic acid may comprise the same or different substituent.

In one embodiment of the present invention, the succinic acid molecule of the at least one mono-substituted succinic acid and the succinic anhydride molecule of the at least one mono-substituted succinic anhydride are mono-substituted with the same group selected from any linear, branched, aliphatic or cyclic group having a total amount of carbon atoms from C2 to C30, preferably from C3 to C20 and most preferably from C4 to C18 in the substituent.

If the at least one mono-substituted succinic anhydride is provided in combination with at least one mono-substituted succinic acid, the at least one mono-substituted succinic acid is present in an amount of ≤10 mol.-%, based on the molar sum of the at least one mono-substituted succinic anhydride and the at least one mono-substituted succinic acid. For example, the at least one mono-substituted succinic acid is present in an amount of ≤5 mol.-%, preferably of ≤2.5 mol.-% and most preferably of ≤1 mol.-%, based on the molar sum of the at least one mono-substituted succinic anhydride and the at least one mono-substituted succinic acid.

According to one embodiment the salty reaction product(s) of the mono-substituted succinic acid and/or the at least one mono-substituted succinic anhydride formed on the surface of said at least one calcium carbonate-comprising filler material are one or more calcium salts and/or one or more magnesium salts thereof.

According to one embodiment the molar ratio of the at least one mono-substituted succinic anhydride and the optional at least one mono-substituted succinic acid to the salty reaction product(s) thereof is from 99.9:0.1 to 0.1:99.9, preferably from 70:30 to 90:10.

According to one embodiment the salty reaction product(s) of the mono-substituted succinic acid and/or the at least one mono-substituted succinic anhydride are one or more calcium and/or magnesium salts thereof.

Thus, it is appreciated that the at least one calcium carbonate-comprising filler material comprises, and preferably consists of, at least one calcium carbonate-comprising filler material and a treatment layer comprising at least one mono-substituted succinic anhydride and/or at least one mono-substituted succinic acid and/or salty reaction product(s) thereof. The treatment layer is formed on the surface of said at least one calcium carbonate-comprising filler material.

In case the treatment layer on the surface of the at least one calcium carbonate-comprising filler material comprises at least one mono-substituted succinic acid, it is preferred that the at least one mono-substituted succinic acid is formed from the applied at least one mono-substituted succinic anhydride. That is to say, the substituent of the at least one mono-substituted succinic acid and the substituent of the at least one mono-substituted succinic anhydride are the same.

Additionally or alternatively, the at least one mono-substituted succinic acid is provided in a blend together with the at least one mono-substituted succinic anhydride.

In one embodiment of the present invention, the treatment layer formed on the surface of the at least one calcium carbonate-comprising filler material comprises the at least one mono-substituted succinic anhydride and at least one mono-substituted succinic acid or salty reaction product(s) thereof obtained from contacting the at least one calcium carbonate-comprising filler material with the at least one mono-substituted succinic anhydride and the optional at least one mono-substituted succinic acid. Alternatively, the treatment layer formed on the surface of the at least one calcium carbonate-comprising filler material comprises the at least one mono-substituted succinic anhydride and at least one mono-substituted succinic acid and salty reaction product(s) thereof obtained from contacting the at least one calcium carbonate-comprising filler material with the at least one mono-substituted succinic anhydride and the optional at least one mono-substituted succinic acid.

It is one requirement of the present invention that the surface-treated filler material comprises the treatment layer in an amount from 0.1 to 3 wt.-%, based on the total dry weight of the at least one calcium carbonate-comprising filler material.

According to one embodiment the surface-treated filler material comprises the treatment layer in an amount of from 0.1 to 2.5 wt.-%, preferably in an amount of from 0.1 to 2 wt.-%, more preferably in an amount of from 0.1 to 1.5 wt.-%, even more preferably in an amount of from 0.1 to 1 wt.-% and most preferably in an amount of from 0.2 to 0.8 wt.-% based on the total dry weight of the at least one calcium carbonate-comprising filler material.

The treatment layer is preferably characterized in that the total weight of the at least one mono-substituted succinic anhydride and/or at least one mono-substituted succinic acid and/or salty reaction product(s) thereof on the surface of the surface-treated filler material is from 0.05 to 1 wt.-%/m$^2$, more preferably from 0.1 to 0.5 wt.-%/m$^2$ and most preferably from 0.15 to 0.25 wt.-%/m$^2$ of the at least one calcium carbonate-comprising filler material.

In one embodiment of the present invention, the treatment layer is characterized in that the total weight of the at least one mono-substituted succinic anhydride and/or mono-substituted succinic acid and/or salty reaction product(s) thereof and the optional at least one organic material on the surface of the surface-treated filler material is from 0.1 to 5 mg/m$^2$, more preferably from 0.25 to 4.5 mg/m$^2$ and most preferably from 1.0 to 4.0 mg/m$^2$ of the at least one calcium carbonate-comprising material.

Additionally or alternatively, the treatment layer of the surface-treated filler material comprises the at least one mono-substituted succinic anhydride and the at least one mono-substituted succinic acid and/or salty reaction product(s) thereof in a specific molar ratio. For example, the molar ratio of the at least one mono-substituted succinic anhydride and the at least one mono-substituted succinic acid to the salty reaction product(s) thereof is from 99.9:0.1 to 0.1:99.9, preferably from 70:30 to 90:10.

The wording "molar ratio of the at least one mono-substituted succinic anhydride and the at least one mono-substituted succinic acid to the salty reaction product(s) thereof" in the meaning of the present invention refers to the sum of the molecular weight of the at least one mono-substituted succinic anhydride and the sum of the molecular weight of the at least one mono-substituted succinic acid to the sum of the molecular weight of the mono-substituted succinic anhydride molecules in the salty reaction products thereof and the sum of the molecular weight of the mono-substituted succinic acid molecules in the salty reaction products thereof.

The surface-treated filler material according to the present invention has excellent surface characteristics in comparison to mineral fillers treated with fatty acids and/or fatty acid salts having at least 10 chain carbon atoms, i.e. without the implementation of the at least one mono-substituted succinic anhydride and the optional at least one mono-substituted succinic acid.

Furthermore, the surface-treated filler material features a low water pick up susceptibility. It is preferred that the moisture pick up susceptibility of the surface-treated filler material is such that its total surface moisture level is less than 1 mg/g of dry calcium carbonate-comprising filler material, at a temperature of about +23° C. (±2° C.). For example, the surface-treated filler material has a moisture pick up susceptibility of from 0.1 to 1 mg/g, more preferably of from 0.2 to 0.9 mg/g and most preferably of from 0.2 to 0.8 mg/g of dry calcium carbonate-comprising material after at a temperature of +23 C (±2° C.).

Additionally or alternatively, the surface-treated filler material has a hydrophilicity of below 8:2 volumetric ratio of water:ethanol measured at +23° C. (±2° C.) with the sedimentation method. For example, the surface-treated filler material has a hydrophilicity of below 7:3 volumetric ratio of water:ethanol measured at +23° C. (±2° C.) with the sedimentation method.

As a non-limiting example, methods for preparing the surface-treated filler material are described, e.g., in WO 2014/060286 A1.

The present inventors found that the inventive treatment layer is crucial for eventually obtaining the inventive breathable film having the desired characteristics. In particular, it was discovered that reducing the particle size of the calcium carbonate-comprising filler material by itself was insufficient for obtaining breathable films having the desired characteristics in a stable process. Rather, it was found that, despite the presence of a fatty acid and/or fatty acid salt having at least 10 chain carbon atoms, e.g., stearic acid, as a treatment layer on the calcium carbonate-comprising filler material, thin breathable films could not be produced in a stable process. Furthermore, the WVTR and the hydrostatic pressure of the so-obtained breathable films were inferior. This was attributed to the formation of agglomerates of the surface-treated filler material, which led to a sharp rise in the extruder pressure and to the formation of large voids in the film. The use of the inventive treatment layer prevents the formation of agglomerates and enables the stable production of the inventive breathable films.

It is appreciated that the particle size distribution of the at least one calcium carbonate-comprising filler material is not altered or are only slightly altered by the surface-treatment. Thus, the surface-treated filler material has

- i) a weight median particle size $d_{50}$ from 0.1 to 7 μm, preferably from 0.25 μm to 5 μm, more preferably from 0.5 μm to 4 μm and most preferably from 0.6 μm to 1 μm, and
- ii) a top cut ($d_{98}$) of ≤15 μm, preferably of ≤12.5 μm, more preferably of ≤10 μm, still more preferably of ≤7.5 μm and most preferably of ≤3 μm, and
- iii) a fineness (<0.5 μm) such that at least 15 wt.-%, preferably at least 20 wt.-%, even more preferably at least 25 wt.-% and most preferably at least 30 wt.-% of all particles have a particle size of <0.5 μm.

For example, the surface-treated filler material has

- i) a weight median particle size $d_{50}$ from 0.6 μm to 1 μm, and
- ii) a top cut ($d_{98}$) of ≤10 μm, preferably of ≤7.5 μm and most preferably of ≤3 μm, and
- iii) a fineness (<0.5 μm) such that at least 20 wt.-%, preferably at least 25 wt.-% and most preferably at least 30 wt.-% of all particles have a particle size of <0.5 μm.

Consequently, in a preferred embodiment, the surface-treated filler material comprises

- A) at least one calcium carbonate-comprising filler material having
  - i) a weight median particle size $d_{50}$ from 0.25 μm to 5 μm, preferably from 0.5 μm to 4 μm and most preferably from 0.6 μm to 1 μm, and
  - ii) a top cut ($d_{98}$) of ≤12.5 μm, preferably of ≤10 μm, more preferably of ≤7.5 μm and most preferably of ≤3 μm, and
  - iii) a fineness (<0.5 μm) such that at least 15 wt.-%, preferably at least 20 wt.-%, even more preferably at least 25 wt.-% and most preferably at least 30 wt.-% of all particles have a particle size of <0.5 μm, and
- B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

Most preferably, the surface-treated filler material comprises

- A) at least one calcium carbonate-comprising filler material having
  - i) a weight median particle size $d_{50}$ from 0.6 μm to 1 μm, and
  - ii) a top cut ($d_{98}$) of ≤10 μm, preferably of ≤7.5 μm and most preferably of ≤3 μm, and
  - iii) a fineness (<0.5 μm) such that at least 20 wt.-%, preferably at least 25 wt.-% and most preferably at least 30 wt.-% of all particles have a particle size of <0.5 μm, and
- B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

According to one embodiment, the breathable film comprises the surface-treated filler material in an amount from 1 to 85 wt.-%, based on the total weight of the breathable film, preferably from 2 to 80 wt.-%, more preferably from 5 to 75 wt.-%, even more preferably from 10 to 65 wt.-%, and most preferably from 15 wt.-% to 60 wt.-%.

According to one aspect of the present invention, the surface-treated filler material described above is used as filler in a breathable film.

The Breathable Film

In a first aspect of the present invention, a breathable film comprising at least one thermoplastic polymer and a surface-treated filler material is provided, wherein the surface-treated filler material comprises A) at least one calcium carbonate-comprising filler material having
   - a weight median particle size $d_{50}$ in the range from 0.1 μm to 7 μm,
   - a top cut particle size des of ≤15 μm,
   - a fineness (<0.5 μm) such that at least 15 wt.-% of all particles have a particle size of <0.5 μm, and
   - a residual total moisture content of ≤1 wt.-%, based on the total dry weight of the at least one calcium carbonate-comprising filler material, and B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

It is appreciated that the breathable film especially features a low basis weight. Thus, the breathable film has a basis weight from 1 to 15 g/m$^2$, or from 4 to 15 g/m$^2$, preferably from 6 to 15 g/m$^2$. In one embodiment, the breathable film has a basis weight from 4 to 13 g/m$^2$, preferably from 6 to 12 g/m$^2$, more preferably from 7 to 10 g/m$^2$, and most preferably about 8 g/m$^2$.

Additionally, in an optional embodiment, the thickness of the breathable film is from 4 to 15 μm, preferably from 6 to 15 μm.

It is appreciated that the thermoplastic polymer and the surface-treated filler material are described in detail hereinabove.

The breathable film is advantageous as it provides a low basis weight at high mechanical properties while maintaining suitable WVTR and hydrostatic pressure values. Furthermore, the breathable film can be produced in a stable process.

For example, at a basis weight of 10 g/m$^2$, the breathable film has a maximum tensile force in machine direction, measured according to ISO 527-3:2018, in the range from 4 to 40 N, more preferably in the range from 4 to 35 N and most preferably in the range from 4 to 35 N.

If the at least one thermoplastic polymer comprises a polyethylene, e.g. a LLDPE, the breathable film, at a basis weight of 10 g/m$^2$, has preferably a maximum tensile force in machine direction, measured according to ISO 527-3:2018, in the range from 4 to 15 N, and more preferably in the range from 6 to 14 N.

If the at least one thermoplastic polymer comprises a polypropylene, the breathable film, at a basis weight of 10 g/m$^2$, has preferably a maximum tensile force in machine direction, measured according to ISO 527-3:2018, in the range from 10 to 30 N, more preferably in the range from 14 to 25 N and most preferably in the range from 20 to 23 N.

Additionally or alternatively, at a basis weight of 10 g/m$^2$, the breathable film has a modulus of elasticity, measured according to ISO 527-3:2018, in the range from 100 to 2 500 N/mm$^2$, and most preferably in the range from 200 to 2 400 N/mm$^2$.

If the at least one thermoplastic polymer comprises a polyethylene, e.g. a LLDPE, the breathable film, at a basis weight of 10 g/m$^2$, has preferably a modulus of elasticity, measured according to ISO 527-3:2018, in the range from 100 to 1 000 N/mm$^2$, and most preferably in the range from 200 to 700 N/mm$^2$.

If the at least one thermoplastic polymer comprises a polypropylene, the breathable film, at a basis weight of 10 g/m$^2$, has preferably a modulus of elasticity, measured according to ISO 527-3:2018, in the range from 1 000 to 2 500 N/mm$^2$, more preferably in the range from 1 100 to 2 400 N/mm$^2$ and most preferably in the range from 2 000 to 2 300 N/mm$^2$.

Additionally or alternatively, at a basis weight of 10 g/m$^2$, the breathable film has a hydrostatic pressure, measured in accordance with the method outlined in the example section, in the range from 50 to 700 mbar, and most preferably in the range from 75 to 600 mbar.

If the at least one thermoplastic polymer comprises a polyethylene, e.g. a LLDPE, the breathable film, at a basis weight of 10 g/m$^2$, has preferably a hydrostatic pressure, measured in accordance with the method outlined in the example section, in the range from 75 to 500 mbar, and most preferably in the range from 150 to 350 mbar.

If the at least one thermoplastic polymer comprises a polypropylene, the breathable film, at a basis weight of 10 g/m$^2$, has preferably a hydrostatic pressure, measured in accordance with the method outlined in the example section, in the range from 100 to 700 mbar, more preferably in the range from 300 to 600 mbar and most preferably in the range from 400 to 500 mbar.

Furthermore, it is appreciated that the breathable film has a good surface quality and a reduced potential of skin irritation.

The breathability of the breathable film can be measured by its water vapour transmission rate. According to one embodiment the breathable film has a water vapour transmission rate (WVTR) from 500 to 10 000 g/(m$^2$·day), preferably from 750 to 8 000 g/(m$^2$·day), and more preferably from 1 000 to 7 000 g/(m$^2$·day), measured with a Lyssy L80-5000 measuring device according to ASTM 398-20.

According to one embodiment, the breathable film has a hydrostatic pressure from 100 to 500 mbar, preferably from 200 to 400 mbar, and more preferably from 250 to 350 mbar, measured with a FX 3000 Hydrotester according to the method which are described above.

The breathable film can comprise the at least one thermoplastic polymer in an amount of at least 15 wt.-%, based on the total weight of the breathable film, preferably of at least 20 wt.-%, more preferably of at least 30 wt.-%, and most preferably at least 40 wt.-%, for example, about 50 wt.-%. According to one embodiment, the breathable film comprises the at least one thermoplastic polymer in an amount from 15 to 70 wt.-%, preferably from 20 to 70 wt.-%, more preferably from 30 to 65 wt.-%, and most preferably from 40 to 60 wt.-%, based on the total weight of the breathable film.

According to one embodiment, the breathable film comprises the surface-treated filler material in an amount from 1 to 85 wt.-%, based on the total weight of the breathable film, preferably from 2 to 80 wt.-%, more preferably from 5 to 75 wt.-%, even more preferably from 10 to 65 wt.-%, and most preferably from 15 wt.-% to 60 wt.-%.

According to one embodiment, the breathable film further comprises additives selected from the group consisting of UV-absorbers, light stabilizers, processing stabilizers, antioxidants, heat stabilizers, nucleating agents, metal deactivators, impact modifiers, plasticizers, lubricants, rheology modifiers, processing aids, pigments, dyes, optical brighteners, antimicrobials, antistatic agents, slip agents, anti block agents, coupling agents, dispersants, compatibilizers, oxygen scavengers, acid scavengers, markers, antifogging agents, surface modifiers, flame retardants, blowing agents, smoke suppressors, reinforcement agents, such as glass fibres, carbon fibres and/or glass bubbles, or mixtures of the foregoing additives.

Preferably, the additives are selected from the class of acid scavengers based on salts of long chain carboxylic acids, such as calcium stearate, magnesium stearate, zinc stearate, and calcium lactate, or may be hydrotalcite, from the class of stabilizers based on phenolic antioxidants, benzofuranones, hydroxylamines, nitrones, thiosynergists, and phosphites/phosphonites, from the class of light stabilizers based on hindered amines (HALS), from the class of metal deactivators, from the class of dispersing agents, coupling agents, or compatibilizers, or a mixture of any of the foregoing additives.

Suitable phenolic antioxidants are, for example: Octadecyl-3-(3,5-di-tert-butyl-4-hydroxyphenyl)propanonate, pentaerythritol-tetrakis[3-(3,5-di-tert-butyl-4-hydroxyphenyl)propanoate, tris(3,5-di-tert-butyl-4-hydroxyphenyl)isocyanurate, 1,3,5-trimethyl-2,4,6-tris(3,5-di-tert-butyl-4-hydroxybenzyl)benzene, triethyleneglycol-bis[3-(3-tert-butyl-4-hydroxy-5-methylphenyl)propanoate, N,N'-hexane-1,6-diyl-bis[3-(3,5-di-tert-butyl-4-hydroxyphenyl)propanamide Suitable phosphites/phosphonites are, for example: Tris-(2,4-di-tertbutylphenyl)phosphite, 3,9-bis(2,4-di-tert-butylphenoxy)-2,4,8,10-tetraoxa-3,9-diphosphaspiro[5.5] undecene, tetrakis(2,4-di-tert-butylphenyl)[1,1-biphenyl]-4,4'-diylbisphosphonite.

Suitable sterically hindered amines are, for example: 1,1-Bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)-n-butyl-3,5-di-tert-butyl-4-hydroxybenzylmalonate, the condensation product of 1-(2-hydroxyethyl)-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinon), 4-benzoyl-2,2,6,6-tetramethylpiperidine, 4-stearyloxy-2,2,6,6-tetramethylpiperidine, linear or cyclic condensation products of N,N'-bis(2,2,6,6-tetramethyl-4-piperidyl)hexamethylenediamine and 4 -morpholino-2,6-dichloro-1,3,5-triazine, the reaction product of 7,7,9,9-tetramethyl-2-cycloundecyl-1-oxa-3,8-diaza-4-oxospiro[4.5]decene and epichlorohydrine.

Suitable dispersants are, for example: Polyacrylates, such as copolymers with long side chains, and polyacrylate block copolymers; alkylamides, such as N,N'-1,2-ethanediylbisoctadecaneamide; sorbitan esters, such as monostearylsorbitan ester; titanates und zirconates; reactive copolymers, such as polypropylene-acrylic acid copolymer; polypropylene-maleic anhydride copolymer; polyethylene-glycidylmethacrylate copolymer; polystyrol-maleic anhydride-polysiloxane alternating copolymer, such as dimethylsilanediol-ethyleneoxide copolymer; polyphenylsiloxan copolymer; amphiphilic copolymers, such as polyethylene-polyethyleneoxide block copolymer; and dendrimers, such as hydroxy containing dendrimers.

A suitable metal deactivator may be, for example, N,N'-bis(3,5-di-tert-butyl-4-hydroxyphenylpropionyl)hydrazine. According to another embodiment, the metal deactivator may be selected from one or more of N'1,N'12-bis(2-hydroxybenzoyl)dodecanedihydrazide (CAS Registry number 63245-38-5) and 2-{[(2-{[3-(3,5-di-tert-butyl-4-hydroxyphenyl)propanoyl]oxy}ethyl)carbamoyl] formamido}ethyl 3-(3,5-di-tert-butyl-4-hydroxyphenyl) propanoate.

According to a preferred embodiment, the breathable film comprises at least one thermoplastic polymer and a surface-treated filler material, wherein the surface-treated filler material comprises A) at least one calcium carbonate-comprising filler material having
   i) a weight median particle size $d_{50}$ from 0.25 μm to 5 μm, preferably from 0.5 μm to 4 μm and most preferably from 0.6 μm to 1 μm, and
   ii) a top cut ($d_{98}$) of ≤12.5 μm, preferably of ≤10 μm, more preferably of ≤7.5 μm and most preferably of ≤3 μm, and
   iii) a fineness (<0.5 μm) such that at least 15 wt.-%, preferably at least 20 wt.-%, even more preferably at least 25 wt.-% and most preferably at least 30 wt.-% of all particles have a particle size of <0.5 μm, and
B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

According to a preferred embodiment, the breathable film comprises at least one thermoplastic polymer and a surface-treated filler material, wherein the surface-treated filler material comprises A) at least one calcium carbonate-comprising filler material having
   i) a weight median particle size $d_{50}$ from 0.6 μm to 1 μm, and
   ii) a top cut ($d_{98}$) of ≤10 μm, preferably of ≤7.5 μm and most preferably of ≤3 μm, and
   iii) a fineness (<0.5 μm) such that at least 20 wt.-%, preferably at least 25 wt.-% and most preferably at least 30 wt.-% of all particles have a particle size of <0.5 μm, and
B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

The breathable film of the present invention may be produced by any method known in the art. Preferably, the inventive breathable film is produced by a process as described hereinbelow.

The Inventive Method

A second aspect of the present invention relates to a process for producing the inventive breathable film. The process for producing a breathable film comprises the steps of:

a) providing a composition comprising at least one thermoplastic polymer and a surface-treated filler material, and b) forming a film from the composition of step a), and c) stretching the film obtained in step b) into at least one direction, wherein the surface-treated filler material comprises A) at least one calcium carbonate-comprising filler material having a weight median particle size $d_{50}$ in the range from 0.1 μm to 7 μm, a top cut particle size $d_{98}$ of ≤15 μm, a fineness (<0.5 μm) such that at least 15 wt.-% of all particles have a particle size of <0.5 μm, and a residual total moisture content of ≤1 wt.-%, based on the total dry weight of the at least one calcium carbonate-comprising filler material, and B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

It is appreciated that the thermoplastic polymer and the surface-treated filler material have been described in detail hereinabove.

The composition of the at least one thermoplastic polymer and the surface-treated filler material provided in process step a) can be produced by mixing or compounding said components. The at least one thermoplastic polymer and the surface-treated filler material, and, if present, other optional additives, may be mixed by the use of a suitable mixer, e.g. a Henschel mixer, a super mixer, a tumbler type mixer or the like. The compounding step may be done with a suitable extruder, preferably by a twin screw extruder (co- or counter-rotating) or by any other suitable continuous compounding equipment, e.g. a continuous co-kneader (Buss), a continuous mixer (Farrel Pomini), a ring extruder (Extricom) or the like. The continuous polymer mass from extrusion may be either pelletized by (hot cut) die face pelletizing with underwater pelletizing, eccentric pelletizing and water ring pelletizing or by (cold cut) strand pelletizing with underwater and conventional strand pelletizing to form the extruded polymer mass into pellets.

Optionally, the compounding step may also be performed with a discontinuous or batch process using an internal (batch) mixer, e.g. a Banburry mixer (HF Mixing Group) or a Brabender mixer (Brabender) or the like.

According to an optional embodiment, the composition provided in process step a) further comprises one or more of the additives described above.

According to one embodiment, the composition provided in process step a) is a masterbatch. According to a preferred embodiment the masterbatch comprises the surface-treated filler material in an amount of from 50 to 85 wt.-%, preferably from 60 to 85 wt.-% and more preferably from 70 to 80 wt.-%, based on the total weight of the masterbatch. The masterbatch may be in form of pellets, beads, or granules.

According to one embodiment of the present invention, the composition provided in step a) is a masterbatch or a compound obtained by mixing and/or kneading the at least one thermoplastic polymer and the surface-treated filler material to form a mixture and continuously pelletizing the obtained mixture under water. Continuously means at least 8 hours, preferably at least 24 hours and more preferably more than 170 hours without interruption.

The inventors of the present invention found that the use of the surface-treated filler material of the present invention in breathable films results in a very finely and homogenously filled breathable film material. Without wishing to be bound to any theory, it is believed that the specific properties of the surface-treated filler material according to the present invention render it especially suitable for application in breathable films, which require having the fillers distributed through the film as uniformly as possible, in order to obtain a the desired properties (i.e., high water vapour permeability, high resistance to liquid penetration, high mechanical properties and suitable machinability).

In a preferred embodiment, the masterbatch has a melt flow rate (190° C., 2.16 kg) in the range from 1 to 20 g/10 min, preferably from 2 to 15 g/10 min, more preferably from 2.5 to 10 g/10 min and most preferably from 3 to 7 g/10 min.

In another preferred embodiment, the masterbatch has a moisture content in the range from 1 to 1000 ppm, preferably 5 to 750 ppm, more preferably 50 to 500 ppm, based on the total weight of the masterbatch, determined with a Brabender Aquatrac+ equipment at 190° C.

The masterbatch may be used directly in process step b) or may be mixed with one or more thermoplastic polymers before process step b). The masterbatch can also be mixed with one or more of the additives described above. According to a preferred embodiment, the masterbatch is used directly in process step b).

The process step b) may be carried out by any well-known techniques used for preparing polymer films. Examples of suitable film extrusion techniques are blown film extrusion or cast film extrusion.

In process step c) the film obtained in process step b) is stretched into at least one direction. During the stretching step, the polymer is partially delaminated from the surface of the surface-treated filler material, whereby pores can be formed in the breathable film. The stretching step c) may be carried out by any means known in the art.

The film can be stretched in at least a uniaxial direction at a temperature from room temperature to the softening point of the thermoplastic polymer by well-known techniques such as a roll method, an interdigitizing method, or a tenter method.

According to one embodiment, in process step c) the film obtained in step b) is stretched by machine direction orientation (MDO). As known to the skilled person, the MDO process consists of a series of stages such as preheating, orienting, annealing and cooling. Typically, the film enters the MDO and is preheated to the required orientation temperature. In the orienting stage, the film is nipped between a slow and a fast, rotating roller. Depending on the desired film properties, the film can be quenched or annealed after orientation. In the final stage, the film may be cooled to near ambient temperature.

The stretching may be carried out by one step or by several steps. According to one embodiment, process step c) is carried out from 1 to 10 times.

Stretch magnification determines film breakage at high stretching as well as breathability and the water vapour transmission of the obtained film, and so excessively high stretch magnification and excessively low stretch magnification are desirably avoided. According to one embodiment, in process step c), the film obtained in step b) is stretched to a stretch magnification from 1.2 to 9 times, more preferably 3 to 8 times into at least one direction. In a preferred embodiment, the stretching ratio (also termed stretching factor or stretching magnification) is defined as the ratio of the speed of the final roll of a stretching unit versus the speed of the first roll thereof.

According to one embodiment in step c) of the inventive process, the film obtained in step b) is stretched in two directions. If biaxial stretching is carried out, it is possible that for example stretching in a first direction is applied in the machine direction or a direction perpendicular thereto, and stretching in a second direction is then applied at right angles to the first direction. Alternatively, the biaxial stretching may be carried out simultaneously in the machine direction and the direction perpendicular thereto.

According to one embodiment, process step c) is carried out at a temperature of about 30 to 160° C., preferably from 40 to 130° C., more preferably from 45 to 80° C., and most preferably from 50 to 70° C.

After the stretching, a heat setting treatment may be carried out if required in order to stabilize the structure of the breathable film. The heat setting treatment may be, for example, a heat setting treatment at a temperature in the range of from the softening point of the polymer to a temperature less than about the melting point of the polymer for a period of 0.1 to 100 s.

The inventors of the present invention found that the breathable film according to the present invention retains good breathability, high resistance to liquid penetration, low film defect levels and good mechanical properties. Furthermore, the breathable film may provide good colour properties and good processing characteristics such as low die build-up properties and a negligible pressure increase during the extrusion.

The Inventive Use

A third aspect of the present invention relates to the use of a surface-treated filler material as a filler in a breathable film having a basis weight from 1 to 15 g/m$^2$, the breathable film comprising at least one thermoplastic polymer, wherein the surface-treated filler material comprises A) at least one calcium carbonate-comprising filler material having
  - a weight median particle size $d_{50}$ in the range from 0.1 μm to 7 μm,
  - a top cut particle size $d_{98}$ of ≤15 μm,
  - a fineness (<0.5 μm) such that at least 15 wt.-% of all particles have a particle size of <0.5 μm, and
  - a residual total moisture content of ≤1 wt.-%, based on the total dry weight of the at least one calcium carbonate-comprising filler material, and B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

It is appreciated that the thermoplastic polymer and the surface-treated filler material are described in detail hereinabove.

In a preferred embodiment, the at least one calcium carbonate-comprising filler material is natural ground calcium carbonate, precipitated calcium carbonate, surface-reacted calcium carbonate, or a mixture thereof, and preferably natural ground calcium carbonate.

In a preferred embodiment, the at least one thermoplastic polymer is a polyolefin, preferably selected from the group consisting of polypropylene, polyethylene, polybutylene, and mixtures thereof, and more preferably selected from the group consisting of high density polyethylene (HDPE), linear low density polyethylene (LLDPE), low density polyethylene (LDPE), ultra-low density polyethylene (ULDPE), very low density polyethylene (VLDPE), and mixtures thereof.

In a preferred embodiment, the breathable film comprises the surface-treated filler material in an amount from 1 to 85 wt.-%, based on the total weight of the breathable film, preferably from 2 to 80 wt.-%, more preferably from 5 to 75 wt.-%, even more preferably from 10 to 65 wt.-%, and most preferably from 15 wt.-% to 60 wt.-%.

In a preferred embodiment, the at least one calcium carbonate-comprising filler material has
- a weight median particle size $d_{50}$ from 0.25 μm to 5 μm, preferably from 0.5 μm to 4 μm, and most preferably from 0.6 μm to 1 μm, and/or
- a top cut particle size $d_{98}$ of ≤12.5 μm, preferably of ≤10 μm, more preferably of ≤7.5 μm, and most preferably of ≤3 μm, and/or
- a fineness (<1 μm) such that at least 70 wt.-%, even more preferably at least 75 wt.-% and most preferably at least 80 wt.-% of all particles have a particle size of ≤1 μm, and/or
- a fineness (<0.5 μm) such that at least 20 wt.-%, preferably at least 25 wt.-%, and most preferably at least 30 wt.-% of all particles have a particle size of <0.5 μm.

In a preferred embodiment, the at least one calcium carbonate-comprising filler material has a specific surface area (BET) of from 0.5 to 150 m$^2$/g, preferably of from 1 to 50 m$^2$/g, more preferably of from 2 to 35 m$^2$/g, and most preferably of from 4 to 15 m$^2$/g, as measured using nitrogen and the BET method according to ISO 9277.

In a preferred embodiment, the at least one calcium carbonate-comprising filler material has a residual total moisture content of from 0.01 to 0.2 wt.-%, preferably from 0.02 to 0.15 wt.-%, and most preferably from 0.04 to 0.15 wt.-%, based on the total dry weight of the at least one calcium carbonate-comprising filler material.

In a preferred embodiment, the surface-treated filler material has a moisture pick-up from 0.1 to 1 mg/g, preferably from 0.2 to 0.9 mg/g, and most preferably from 0.2 to 0.8 mg/g, at a temperature of 23° C. (±2° C.).

In a preferred embodiment, the at least one mono-substituted succinic anhydride consists of succinic anhydride mono-substituted with a group selected from a linear, branched, aliphatic or cyclic group having a total amount of carbon atoms from C2 to C30, preferably from C3 to C25, and most preferably from C4 to C20 in the substituent.

In a preferred embodiment, the breathable film has a basis weight from 4 to 13 g/m$^2$, preferably from 6 to 12 g/m$^2$, more preferably from 7 to 10 g/m$^2$ and most preferably about 8 g/m$^2$.

In a preferred embodiment, the surface-treated filler material comprises

A) at least one calcium carbonate-comprising filler material having
   i) a weight median particle size $d_{50}$ from 0.25 μm to 5 μm, preferably from 0.5 μm to 4 μm and most preferably from 0.6 μm to 1 μm, and
   ii) a top cut ($d_{98}$) of ≤12.5 μm, preferably of ≤10 μm, more preferably of ≤7.5 μm and most preferably of ≤3 μm, and
   iii) a fineness (<0.5 μm) such that at least 15 wt.-%, preferably at least 20 wt.-%, even more preferably at least 25 wt.-% and most preferably at least 30 wt.-% of all particles have a particle size of <0.5 μm, and
B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

Most preferably, the surface-treated filler material comprises

A) at least one calcium carbonate-comprising filler material having
   i) a weight median particle size $d_{50}$ from 0.6 μm to 1 μm, and
   ii) a top cut ($d_{98}$) of ≤10 μm, preferably of ≤7.5 μm and most preferably of ≤3 μm, and
   iii) a fineness (<0.5 μm) such that at least 20 wt.-%, preferably at least 25 wt.-% and most preferably at least 30 wt.-% of all particles have a particle size of <0.5 μm, and
B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

In a particularly preferred embodiment of the present invention, the surface-treated filler material is used as a filler in a breathable film for improving the water vapour retention rate and/or the hydrostatic pressure and/or the machinability of the breathable film, compared to the same breathable film comprising a surface-treated filler material, which comprises the at least one calcium carbonate-comprising filler material and a treatment layer on the surface of the at least one calcium carbonate-comprising filler material comprising at least one saturated aliphatic linear or branched monocarboxylic acid and salty reaction products thereof. By the term “improving”, it is meant that the water vapour retention rate is increased, the hydrostatic pressure is increased and the pressure increase is minimized, respectively.

By “the same breathable film”, it is meant that a breathable film comprising the surface-treated filler material, which comprises the at least one calcium carbonate-comprising filler material and a treatment layer on the surface of the at least one calcium carbonate-comprising filler material comprising at least one saturated aliphatic linear or branched monocarboxylic acid and salty reaction products thereof instead of the inventive treatment layer, all else being equal, is produced in the same way as the inventive breathable film, i.e., following the same method steps for its production and using the same remaining compounds in the same relative amounts other than the replaced material (i.e., the treatment layer).

For the purposes of the present invention, the water vapour retention rate is determined according to ASTM E398-20.

Furthermore, the hydrostatic pressure is determined according to AATCC Test Method 127-2013, WSP 80.6 or DIN EN ISO 811:2018-08, as outlined in detail herein.

For the purposes of the present invention, the machinability is measured as a pressure increase observed in an extruder when producing the breathable film for 1 h and 5 min, wherein the pressure increase is measured by producing the breathable film by extruding a composition comprising the surface-treated filler material and the at least one thermoplastic polymer in a single screw extruder having a temperature profile of 195° C.-210° C.-230° C.-230° C., a rotation speed of the extruder screw of 35 rpm, a screw diameter of 30 mm and a die gap of 0.85 mm, wherein the pressure increase is defined as the difference of the initial pressure and the final pressure, measured in the extruder before the melt filter, wherein the initial pressure is measured 5 minutes after a melt filter with 42 micron mesh size is placed against the breaker plate between the extruder screw tip and the die, and wherein the final pressure is measured after 1 h and 5 min of producing the breathable film in the presence of the melt filter. The single screw extruder may be a single screw extruder manufactured by Dr. Collin GmbH (Collin Lab & Pilot Solutions GmbH).

Thus, the composition comprising the at least one thermoplastic polymer and the surface-treated filler material is molten and mixed in the single screw extruder. After having passed the extruder screw tip, the molten mixture then passes through the melt filter, the breaker plate and the die. The pressure may be measured by any means known to the skilled person, e.g., by a pressure transducer, such as a strain gage transducer, a piezo-electric transducer and a pneumatic pressure transducer, and a melt pressure gauge. The melt filter preferably is a screen pack.

For example, the surface-treated filler material is used as a filler in a breathable film for improving the water vapour retention rate and/or the hydrostatic pressure and/or the machinability of the breathable film, compared to the same breathable film comprising a surface-treated filler material, which comprises the at least one calcium carbonate-comprising filler material and a treatment layer on the surface of the at least one calcium carbonate-comprising filler material consisting of stearic acid.

In one embodiment, the inventive surface-treated filler material is used as a filler in a breathable film for improving the water vapour retention rate of the breathable film by at least 5%, preferably at least 10%, more preferably at least 15%, compared to the same breathable film comprising a surface-treated filler material, which comprises the at least one calcium carbonate-comprising filler material and a treatment layer comprising at least one saturated aliphatic linear or branched monocarboxylic acid and salty reaction products thereof.

In one embodiment, the inventive surface-treated filler material is used as a filler in a breathable film for improving the hydrostatic pressure of the breathable film by at least 5%, preferably at least 10%, more preferably at least 15%, compared to the same breathable film comprising a surface-treated filler material, which comprises the at least one calcium carbonate-comprising filler material and a treatment layer comprising at least one saturated aliphatic linear or branched monocarboxylic acid and salty reaction products thereof.

In one embodiment, the surface-treated filler material is used as a filler in a breathable film for reducing the basis weight of the breathable film by at least 10%, preferably at least 15%, more preferably at least 20%, compared to the same breathable film comprising a surface-treated filler material, which comprises the at least one calcium carbonate-comprising filler material and a treatment layer on the surface of the at least one calcium carbonate-comprising filler material comprising at least one saturated aliphatic linear or branched monocarboxylic acid and salty reaction products thereof, wherein the W/TR of the breathable film is at least essentially the same, compared to the same breathable film comprising a surface-treated filler material, which comprises the at least one calcium carbonate-comprising filler material and a treatment layer comprising at least one saturated aliphatic linear or branched monocarboxylic acid and salty reaction products thereof.

By the term "at least essentially the same", it is meant that the WVTR of the inventive breathable film is at least 95% of the WVTR of the comparative breathable film.

In one embodiment, the surface-treated filler material is used as a filler in a breathable film for reducing the basis weight of the breathable film by at least 10%, preferably at least 15%, more preferably at least 20%, compared to the same breathable film comprising a surface-treated filler material, which comprises the at least one calcium carbonate-comprising filler material and a treatment layer comprising at least one saturated aliphatic linear or branched monocarboxylic acid and salty reaction products thereof, wherein the maximum tensile force (MD and/or CD) of the breathable film is at least essentially the same, compared to the same breathable film comprising a surface-treated filler material, which comprises the at least one calcium carbonate-comprising filler material and a treatment layer on the surface of the at least one calcium carbonate-comprising filler material comprising at least one saturated aliphatic linear or branched monocarboxylic acid and salty reaction products thereof.

By the term "at least essentially the same", it is meant that the maximum tensile force (MD and/or CD) of the inventive breathable film is at least 95% of the maximum tensile force (MD and/or CD) of the comparative breathable film. The term "maximum tensile force (MD and/or CD)" designates the maximum tensile force in machine direction and/or the maximum tensile force in cross direction.

In a particularly preferred embodiment, the surface-treated filler material is used as a filler in a breathable film for improving the machinability of the breathable film, compared to the same breathable film comprising a surface-treated filler material, which comprises the at least one calcium carbonate-comprising filler material and a treatment layer comprising at least one saturated aliphatic linear or branched monocarboxylic acid and salty reaction products thereof.

The Inventive Article and Inventive Use of the Breathable Film

In a fourth aspect of the present invention, an article comprising the inventive breathable film having a basis weight from 1 to 15 $g/m^2$ is provided. The article is selected from the group consisting of hygiene products, medical products, healthcare products, filter products, geotextile products, agriculture products, horticulture products, clothing, footwear products, baggage products, household products, industrial products, packaging products, building products, and construction products.

A fifth aspect of the present invention relates to the use of the inventive breathable film having a basis weight from 1 to 15 $g/m^2$ in hygienic applications, medical applications, healthcare applications, filtration materials, geotextile products, agricultural applications, horticultural applications, clothing, footwear products, baggage products, household applications, industrial applications, packaging applications, building applications, or construction.

The inventive breathable film may be especially suitable for hygiene products, such as baby diapers, adult incontinence products, or wound dressings.

Preferably, the hygiene products are selected from the group comprising absorbent hygiene products such as baby diapers or nappies, feminine hygiene, adult incontinence products, depilatory strips, bandages and wound dressings, disposable bath and face towels, disposable slippers and footwear, top sheets or coverstocks, consumer face masks, leg cuffs, acquisition/distribution layers, core wraps, back sheets, stretch ears, landing zones, dusting layers and fastening systems; and wipes such as wet wipes, skin care wipes, baby wipes, facial wipes, cleansing wipes, hand and body wipes, moist towelettes, personal hygiene wipes, feminine hygiene wipes, antibacterial wipes and medicated wipes.

Preferably, the medical and healthcare products are selected from the group comprising medical products which can be sterilized, medical packaging, caps like surgical disposable caps, protective clothing, surgical gowns, surgical masks and face masks, surgical scrub suits, surgical covers, surgical drapes, wraps, packs, sponges, dressings, wipes, bed linen, contamination control gowns, examination gowns, lab coats, isolation gowns, transdermal drug delivery, shrouds, underpads, procedure packs, heat packs, ostomy bag liners, fixation tapes, incubator mattress, sterilisation wraps (CSR wrap), wound care, cold/heat packs, drug delivery systems like patches.

Preferably, the clothing, footwear and baggage products are selected from the group comprising interlinings like fronts of overcoats, collars, facings, waistbands, lapels etc., disposable underwear, shoe components like shoelace eyelet reinforcement, athletic shoe and sandal reinforcement and inner sole lining etc., bag components, bonding agents, composition and (wash) care labels.

Preferably, the packaging products are selected from the group comprising interlinings like desiccant packaging, sorbents packaging, gift boxes, file boxes, nonwoven bags, book covers, mailing envelopes, Express envelopes, courier bags and the like.

Preferably, the building and construction products are selected from the group comprising house wrap, asphalt overlay, road and railroad beds, golf and tennis courts, wallcovering backings, acoustical wall coverings, roofing materials and tile underlayment, soil stabilizers and roadway underlayment, foundation stabilizers, erosion control, canals construction, drainage systems, geomembrane protection, frost protection, agriculture mulch, pond and canal water barriers, and sand infiltration barriers for drainage tile.

The scope and interest of the invention will be better understood based on the following examples which are intended to illustrate certain embodiments of the present invention and are non-limitative.

EXAMPLES

1 Measurement Methods and Materials

In the following, measurement methods and materials implemented in the examples are described.

Particle Size

The particle distribution of the untreated ground calcium carbonate-comprising filler material was measured using a Sedigraph 5120 from the company Micromeritics, USA. The method and the instruments are known to the skilled person and are commonly used to determine grain size of fillers and pigments. The measurement was carried out in an aqueous solution comprising 0.1 wt.-% $Na_4P_2O_7$. The samples were dispersed using a high speed stirrer and supersonics.

Specific Surface Area (BET)

The specific surface area was measured using nitrogen and the BET method according to ISO 9277:2010.

Ash Content

The ash content in [%] of the masterbatches was determined by incineration of a sample in an incineration crucible which is put into an incineration furnace at 570° C. for 2 hours. The ash content is measured as the total amount of remaining inorganic residues.

Melt Flow Rate (MFR)

Melt flow rate of the masterbatches has been determined according to ISO 1133:2011 (190° C., 2.16 kg).

Moisture Aquatrac

Moisture of pellets was determined with a BrabenderAquatrac+ equipment at 190° C. The polymer pellets were preconditioned in a Motan dry air drier MDE 40 for 2 hours at 80° C. Before the measurement in Aquatrac. The Aquatrac equipment measures the pressure caused by the reaction of the evaporated water of the pellets with calcium hydride agent. With the resulting pressure the moisture will be calculated by the equipment. For the measurement the procedure given by the manual was followed.

Film Grammage

Film grammage (also termed gauge or basis weight) was tested by punching out a round 100 $cm^2$ specimen from the film and weigh the specimen. Therefrom, the weight per area (in $g/m^2$, i.e., gsm) can be calculated.

Tensile Properties of the Film

Force at 2% elongation, Force at 5% elongation, maximum tensile force and elongation at break were determined according to ISO 527-3:2018. The width of the film specimen was of 15 mm and the testing length was 5 cm. The specimen were prepared in machine direction and cross direction and the tensile properties were measured in both directions.

Visual Evaluation of the Film

Film samples have been put under a light microscope. Calcium carbonate agglomerates appear black upon illumination from below and white upon illumination from above.

Water Vapour Transmission Rate (WVTR)

The WVTR value of the breathable films was measured with a Lyssy L80-5000 (PBI-Dansensor A/S, Denmark) measuring device according to ASTM E398-20.

Hydrostatic Pressure Test (Water Column)

The hydrostatic pressure test has been carried out according to a procedure which is equivalent to AATCC Test Method 127-2013, WSP 80.6 and ISO 811:2018. A film sample (test area=10 $cm^2$) was mounted to form a cover on the test head reservoir. This film sample was subjected to a standardized water pressure, increased at a constant rate until leakage appears on the outer surface of the film, or water burst occurred as a result of film failure (pressure rate gradient=100 mbar/min.). Water pressure was measured as the hydrostatic head height reached at the first sign of leakage in three separate areas of the film sample or when burst occurs. The head height results were recorded in centimetres or millibars of water pressure on the specimen. A higher value indicated greater resistance to water penetration. The TEXTEST FX-3000, Hydrostatic Head Tester (Textest AG, Switzerland), was used for the hydrostatic pressure measurements.

2 Materials

CC1 (comparative): Natural ground calcium carbonate, commercially available from Omya International AG, Switzerland ($d_{50}$: 1.7 μm; $d_{98}$: 6 μm, content of particles <0.5 μm=12%), surface-treated with 1.0 wt.-% stearic acid (commercially available from Sigma-Aldrich, Croda) based on the total weight of the natural ground calcium carbonate. BET: 3.4 $m^2/g$.

CC2 (comparative): Natural ground calcium carbonate, commercially available from Omya International AG, Switzerland ($d_{50}$: 1.7 μm; $d_{98}$: 6 μm, content of particles <0.5 μm=12%), surface-treated with 0.7 wt.-% alkenyl succinic anhydride (CAS [68784-12-3], concentration >93%) based on the total weight of the natural ground calcium carbonate. BET: 3.4 $m^2/g$ CC3 (comparative): Natural ground calcium carbonate, commercially available from Omya International AG, Switzerland ($d_{50}$: 0.7 μm; $d_{98}$: 3 μm, content of particles <0.5 μm=34%), surface-treated with 1.4 wt.-% stearic acid (commercially available from Sigma-Aldrich, Croda) based on the total weight of the natural ground calcium carbonate. BET: 7.3 $m^2/g$ CC4 (inventive): Natural ground calcium carbonate, commercially available from Omya International AG, Switzerland ($d_{50}$: 0.7 μm; $d_{98}$: 3 μm, content of particles <0.5 μm=34%), surface-treated with 1.7 wt.-% alkenyl succinic anhydride (CAS [68784-12-3], concentration >93%) based on the total weight of the natural ground calcium carbonate. BET: 7.3 $m^2/g$ P1: LLDPE Dowlex 2035G (MFR: 6 g/10 min (190° C., 2.16 kg), density: 0.919 $g/cm^3$ according to technical data sheet), commercially available from The Dow Chemical Company, USA.

P2: LDPE Dow SC 7641 (MFR: 2 g/10 min (190° C., 2.16 kg), density: 0.923 $g/cm^3$ according to technical data sheet), commercially available from The Dow Chemical Company, USA.

3 Examples

Example 1—Preparation of Compounds (CO)

Compounds containing 50 wt.-% CC1 or CC2, respectively, were continuously prepared on a lab scale Buss kneader (PR46 from Buss AG, Switzerland). The obtained compounds were pelletized on a spring load pelletizer, model SLC (Gala, USA) in a water bath having a starting temperature between 20 and 25° C. The compositions and filler contents of the prepared compounds are compiled in Table 1 below. The precise filler content was determined by the ash content.

TABLE 1

| Compositions and properties of prepared compounds. | | | | | | |
|---|---|---|---|---|---|---|
| Compound | Filler | P1 [wt.-%] | P2 [wt.-%] | ash content [wt.-%] | Melt flow rate (190° C., 2.16 kg) [g/10 min] | Moisture Aquatrac at 190° C. [ppm] |
| CO1 | CC1 | 45 | 5 | 49.2 | 3.7 | 179 |
| CO2 | CC2 | 45 | 5 | 49.1 | 4.1 | 200 |
| CO3 | CC3 | 45 | 5 | 49.4 | 4.2 | 326 |
| CO4 | CC4 | 45 | 5 | 49.0 | 4.5 | 327 |

The results shown in Table 1 confirm that compounds with good quality and correct dosing of the calcium carbonate fillers were produced.

Example 2—Preparation of Breathable Films

Breathable films were produced by a pilot-extrusion cast-film line with integrated MDO-II unit (Dr. Collin GmbH, Germany). The polymer compounds were dried for 2 hours at 80° C. in a Motan dry air dryer MD40 before extrusion. The extruder temperature settings were 195° C.-210° C.-230° C.-230° C., and the rotation speed of the extruder screw was 35 rpm, using the compounds of Example 1. The die gap was set at 0.85 mm. When changing the compound sample, the extrusion was run for 15 minutes to purge the former compound. After that a fresh melt filter with 42 micron mesh size was installed and after further 5 minutes the initial pressure before the filter was monitored. The film extrusion was then run for 1 hour and the pressure was measured again. The pressure difference is an indication for the dispersion quality of the compound, and for the machinability, i.e., whether the production process can be considered stable. The chill roll was at 45° C. The speed of the chill roll was at 3 to 5 m/min. It was adjusted to match the desired film grammage. The stretching roll temperature was at 60° C. The stretching ratio of the stretching unit was increased and until a homogeneously stretched film was achieved. The stretching ratio (also termed stretching factor or stretching magnification) is defined as the ratio of the speed of the final roll of the stretching unit of the Dr. Collin MDO-II line versus the speed of the first roll.

The film quality of the obtained breathable films was inspected visually and the films were tested regarding their tensile properties, their water vapor transmission rate (WVTR) and their hydrostatic pressure. The results are shown in Table 2, 3 and 4 below.

TABLE 2

| Compositions and properties of prepared breathable films. | | | | | | | |
|---|---|---|---|---|---|---|---|
| Sample | Compound | Stretching factor | Pressure increase 1 h [bar] | Film grammage [g/m²] | Film quality | WVTR [g/(m² × day)] | Hydrostatic pressure [mbar] |
| 1 | CO1 | 6.2 | 4 | 12 | ok | 3853 | 244 |
| 2 | CO2 | 6.2 | 0 | 12 | ok | 4190 | 203 |
| 3 | CO3 | 7.3 | 18 | 12 | SA* | 4177 | 267 |
| 4 | CO4 | 7.3 | 2 | 12 | ok | 4637 | 308 |
| 5 | CO4 | 7.3 | 2 | 11 | ok | 4702 | 240 |
| 6 | CO4 | 7.3 | 2 | 10 | ok | 4926 | 208 |

*SA means "Some agglomerates"

The results shown in Table 2 confirm that the inventive breathable films 4 to 8 show a good quality and breathability. Film 1 to 4 were produced with 12 gsm basis weight. Film 1 and 2 had lower hydrostatic pressure which is an important parameter for hygiene applications. Film 3 and 4 contain finer carbonate which leads to higher hydrostatic pressure. Film 3 with the fine carbonate and stearic acid coating contained in CO3 showed some unwanted agglomerates and lead to a fast increase in extruder pressure. It was further tried with CO3 to produce films with slightly thinner gauge of 11.5 gsm, but the film broke twice. This may have been caused by void formation at agglomerates. Therefore the film trials with CO3 have been stopped. It was concluded that CO3 does not allow to produce thinner films than 12 gsm. In industrial film extrusion the fast extruder pressure increase would additionally lead to short and instable production runs with CO3, as the production may have to be stopped due to exceeding pressure and a new filter would have to be installed. Surprisingly, Film 4, using CO4 with finer carbonate but the inventive coating, did not show this phenomenon. It would therefore allow long production runs and high hydrostatic pressure at the same time. The good quality allowed to reduce the grammage of the breathable films from 12 gsm subsequently down to 10 gsm and still matching the hydrostatic pressure of the comparative film 2 with 12 gsm. This allows to reduce raw material cost and environmental impact.

TABLE 3

| Compositions and mechanical properties of prepared breathable films. Film samples taken in machine direction (MD). | | | | | |
|---|---|---|---|---|---|
| Sample | Film grammage [g/m²] | Force at 2% [N] | Force at 5% [N] | Max. Force [N] | Max. Elongation [%] |
| 1 | 12 | 1.2 | 2.7 | 9.1 | 13.7 |
| 2 | 12 | 1.2 | 2.5 | 7.4 | 13.6 |
| 3 | 12 | 1.7 | 3.6 | 9.6 | 12.3 |
| 4 | 12 | 1.7 | 3.9 | 10.0 | 11.8 |
| 5 | 11 | 1.5 | 3.3 | 11.7 | 14.6 |
| 6 | 10 | 1.6 | 3.6 | 12.4 | 14.8 |

TABLE 4

| Compositions and mechanical properties of prepared breathable films. Film samples taken in cross direction (CD). | | | | | |
|---|---|---|---|---|---|
| Sample | Film grammage [g/m²] | Force at 2% [N] | Force at 5% [N] | Max. Force [N] | Max. Elongation [%] |
| 1 | 12 | 0.24 | 0.37 | 0.56 | 323 |
| 2 | 12 | 0.23 | 0.36 | 0.58 | 334 |

TABLE 4-continued

Compositions and mechanical properties of prepared breathable films. Film samples taken in cross direction (CD).

| Sample | Film grammage [g/m²] | Force at 2% [N] | Force at 5% [N] | Max. Force [N] | Max. Elongation [%] |
|---|---|---|---|---|---|
| 3 | 12 | 0.28 | 0.44 | 0.64 | 323 |
| 4 | 12 | 0.27 | 0.44 | 0.70 | 316 |
| 5 | 11 | 0.27 | 0.44 | 0.72 | 328 |
| 6 | 10 | 0.29 | 0.43 | 0.63 | 323 |

The mechanical properties of the obtained breathable films, such as force at 2% elongation, force at 5% elongation, maximum tensile force and elongation at break in machine and cross direction, are outlined in Tables 3 and 4.

The mechanical properties are important for processing, for example for the subsequent processing steps, such as printing. Tensile properties in MD are important for film winding. Reasonable properties in CD direction are important to prevent slicing. As can be seen in table 3 and 4 the tensile forces of film 3 but even more of film 4 are higher than those of films 1 and 2. As CO4 allows easy processing the films could be made thinner by reducing the film grammage of films 6, 7 and 8 subsequently from 12 gsm down to 10 gsm. Surprisingly even the thinner films still exceeded the force at 2% elongation, force at 5% elongation and maximum tensile force of the comparative films 1 and 2. Even more surprisingly the thinner but stronger films 6, 7 and 8 did not provide distinctively lower elongation at break, as these films had even higher elongation at break in MD direction and elongations at break in CD direction above 300%.

Example 3—Preparation of Breathable Films

Breathable films were produced by a pilot-extrusion cast-film line with integrated MDO-II unit (Dr. Collin GmbH, Germany) in the same way as in example 2

The film quality of the obtained breathable films was inspected visually and the films were tested regarding their tensile properties and their water vapor transmission rate (WVTR). The results are shown in Table 5, 6 and 7 below.

TABLE 5

Compositions and properties of prepared breathable films.

| Sample | Compound | Stretching factor | Pressure increase 1 h [bar] | Film grammage [g/m²] | Film quality | WVTR [g/(m² × day)] |
|---|---|---|---|---|---|---|
| 7 | CO2 | 5.5 | 0 | 12.5 | ok | 3766 |
| 8 | CO4 | 5.5 | 0 | 12.4 | ok | 3485 |
| 9 | CO4 | 6.4 | 2 | 9.8 | ok | 3160 |
| 10 | CO4 | 6.4 | 2 | 9.1 | ok | 2792 |
| 11 | CO4 | 6.4 | 2 | 7.7 | ok | 3176 |

The results shown in Table 2 confirm that the inventive breathable films 8 to 11 show a good quality and breathability. Film 7 to 8 were produced with around 12 gsm basis weight. Film 9 to 11 were produced with lower basis weight. All films had good breathability suitable for hygiene applications.

TABLE 6

Compositions and mechanical properties of prepared breathable films. Film samples taken in machine direction (MD).

| Sample | Film grammage [g/m²] | Force at 2% [N] | Force at 5% [N] | Max. Force [N] |
|---|---|---|---|---|
| 7 | 12.5 | 1.8 | 3.8 | 10.4 |
| 8 | 12.4 | 2.7 | 6.2 | 13.6 |
| 9 | 9.8 | 2.2 | 5.1 | 10.5 |
| 10 | 9.1 | 1.9 | 4.7 | 9.4 |
| 11 | 7.7 | 1.9 | 4.5 | 9.3 |

TABLE 7

Compositions and mechanical properties of prepared breathable films. Film samples taken in cross direction (CD).

| Sample | Film grammage [g/m²] | Force at 2% [N] | Force at 5% [N] | Max. Force [N] |
|---|---|---|---|---|
| 7 | 12.5 | 0.41 | 0.58 | 0.97 |
| 8 | 12.4 | 0.79 | 0.98 | 0.99 |
| 9 | 9.8 | 0.67 | 0.68 | 0.80 |
| 10 | 9.1 | 0.74 | 0.71 | 0.89 |
| 11 | 7.7 | 0.51 | 0.51 | 0.68 |

The mechanical properties of the obtained breathable films, such as force at 2% elongation, force at 5% elongation and maximum tensile force in machine and cross direction, are outlined in Tables 6 and 7.

The mechanical properties are important for processing, for example for the subsequent processing steps, such as printing. Tensile properties in MD are important for film winding. Reasonable properties in CD direction are important to prevent slicing. As can be seen in table 6 and 7 the tensile forces of film 8 are higher than those of film 7. As CO4 allows easy processing the films could be made thinner by reducing the film grammage of films 9, 10 and 11 subsequently from 12 gsm down to 8 gsm. Surprisingly even the thinner films still exceeded the force at 2% elongation and force at 5% elongation and maximum tensile force of the comparative film 7. This kind of stiffness is important for the further processing of the film. The maximum force stayed on a comparable level even at very low grammage.

The invention claimed is:

1. A breathable film with a basis weight from 1 to 10 g/m², the breathable film comprising at least one thermoplastic polymer and a surface-treated filler material, wherein the surface-treated filler material comprises A) at least one calcium carbonate-comprising filler material having a weight median particle size $d_{50}$ in the range from 0.1 μm to 7 μm, a top cut particle size $d_{98}$ of ≤15 μm, a fineness (<0.5 μm) such that at least 15 wt.-% of all particles have a particle size of <0.5 μm, and a residual total moisture content of ≤1 wt.-%, based on the total dry weight of the at least one calcium carbonate-comprising filler material, and B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material, wherein the at least one thermoplastic polymer is selected from the group consisting of high density polyethylene (HDPE), linear low density polyethylene (LLDPE), low density polyethylene (LDPE), ultra-low density polyethylene (ULDPE), very low density polyethylene (VLDPE), and mixtures thereof.

2. The breathable film of claim 1, wherein the at least one calcium carbonate-comprising filler material is natural ground calcium carbonate, precipitated calcium carbonate, surface-reacted calcium carbonate, or a mixture thereof.

3. The breathable film of claim 1, wherein the at least one calcium carbonate-comprising filler material has a) a weight median particle size $d_{50}$ from 0.6 μm to 1 μm, and/or b) a top cut particle size $d_{98}$ of ≤3 μm.

4. The breathable film of claim 1, wherein the at least one thermoplastic polymer is selected from the group consisting of linear low density polyethylene (LLDPE), low density polyethylene (LDPE), and mixtures thereof.

5. The breathable film of claim 1, wherein the breathable film comprises the surface-treated filler material in an amount from 1 to 85 wt.-%, based on the total weight of the breathable film.

6. The breathable film of claim 1, wherein the breathable film comprises the surface-treated filler material in an amount from 15 wt.-% to 60 wt.-%, based on the total weight of the breathable film.

7. The breathable film of claim 1, wherein the at least one calcium carbonate-comprising filler material has a) a weight median particle size $d_{50}$ from 0.25 μm to 5 μm, and/or b) a top cut particle size $d_{98}$ of ≤12.5 μm, and/or c) a fineness (<1 μm) such that at least 70 wt.-% of all particles have a particle size of <1 μm, and/or d) a fineness (<0.5 μm) such that at least 20 wt.-% of all particles have a particle size of <0.5 μm.

8. The breathable film of claim 1, wherein the at least one calcium carbonate-comprising filler material has i) a fineness (<1 μm) such that at least 80 wt.-% of all particles have a particle size of <1 μm, and/or ii) a fineness (<0.5 μm) such that at least 30 wt.-% of all particles have a particle size of <0.5 μm.

9. The breathable film of claim 1, wherein the at least one calcium carbonate-comprising filler material has a specific surface area (BET) of from 0.5 to 150 $m^2/g$, as measured using nitrogen and the BET method according to ISO 9277:2010.

10. The breathable film of claim 1, wherein the at least one calcium carbonate-comprising filler material has a residual total moisture content of from 0.01 to 0.2 wt.-%, based on the total dry weight of the at least one calcium carbonate-comprising filler material.

11. The breathable film of claim 1, wherein the surface-treated filler material has a moisture pick-up from 0.1 to 1 mg/g, at a temperature of 23° C.(±2° C.).

12. The breathable film of claim 1, wherein the surface-treated filler material has a moisture pick-up from 0.2 to 0.8 mg/g, at a temperature of 23° C.(±2° C.).

13. The breathable film of claim 1, wherein the at least one mono-substituted succinic anhydride consists of succinic anhydride mono-substituted with a group selected from a linear, branched, aliphatic or cyclic group having a total amount of carbon atoms from C2 to C30 in the substituent.

14. The breathable film of claim 1, wherein the film has a basis weight from 4 to 10 $g/m^2$.

15. The breathable film of claim 1, wherein the film has a basis weight of about 8 $g/m^2$.

16. The breathable film of claim 1, wherein the water vapour retention rate and/or the hydrostatic pressure and/or the machinability of the breathable film is increased, compared to the same breathable film comprising a surface-treated filler material, which comprises the at least one calcium carbonate-comprising filler material and a treatment layer on the surface of the at least one calcium carbonate-comprising filler material comprising at least one saturated aliphatic linear or branched monocarboxylic acid and salty reaction products thereof, wherein the water vapour retention rate is determined according to ASTM E398-20, the hydrostatic pressure is determined according to AATCC Test Method 127-2013, WSP 80.6 or DIN EN ISO 811:2018-08, and the machinability is measured as a pressure increase observed in an extruder when producing the breathable film for 1 h and 5 min, wherein the pressure increase is measured by producing the breathable film by extruding a composition comprising the surface-treated filler material and the at least one thermoplastic polymer in a single screw extruder having a temperature profile of 195° C.-210° C.-230° C.-230° C., a screw diameter of 30 mm, a rotation speed of the extruder screw of 35 rpm and a die gap of 0.85 mm, wherein the pressure increase is defined as the difference of the initial pressure and the final pressure, measured in the extruder before the melt filter, wherein the initial pressure is measured 5 minutes after a melt filter with 42 micron mesh size is placed against the breaker plate between the extruder screw tip and the die, and wherein the final pressure is measured after 1 h and 5 min of producing the breathable film.

17. The breathable film of claim 1, wherein the water vapour retention rate is increased by at least 5%, compared to the same breathable film comprising a surface-treated filler material, which comprises the at least one calcium carbonate-comprising filler material and a treatment layer on the surface of the at least one calcium carbonate-comprising filler material comprising at least one saturated aliphatic linear or branched monocarboxylic acid and salty reaction products thereof, wherein the water vapour retention rate is determined according to ASTM E398-20.

18. The breathable film of claim 1, wherein the hydrostatic pressure of the breathable film is increased by at least 5%, compared to the same breathable film comprising a surface-treated filler material, which comprises the at least one calcium carbonate-comprising filler material and a treatment layer on the surface of the at least one calcium carbonate-comprising filler material comprising at least one saturated aliphatic linear or branched monocarboxylic acid and salty reaction products thereof, wherein the hydrostatic pressure is determined according to AATCC Test Method 127-2013, WSP 80.6 or DIN EN ISO 811:2018-08.

19. An article comprising a breathable film with a basis weight from 1 to 15 g/m$^2$ according to claim 1, wherein the article is selected from the group consisting of hygiene products, medical products, healthcare products, filter products, geotextile products, agriculture products, horticulture products, clothing, footwear products, baggage products, household products, industrial products, packaging products, building products, and construction products.

20. A process for producing a breathable film with a basis weight from 1 to 15 g/m$^2$ according to claim 1, comprising the steps of:

a) providing a composition comprising at least one thermoplastic polymer and a surface-treated filler material, and b) forming a film from the composition of step a), and c) stretching the film obtained in step b) in at least one direction, wherein the surface-treated filler material comprises A) at least one calcium carbonate-comprising filler material having a weight median particle size $d_{50}$ in the range from 0.1 μm to 7 μm, a top cut particle size $d_{98}$ of ≤15 μm, a fineness (<0.5 μm) such that at least 15 wt.-% of all particles have a particle size of <0.5 μm, and a residual total moisture content of ≤1 wt.-%, based on the total dry weight of the at least one calcium carbonate-comprising filler material, and B) a treatment layer on the surface of the at least one calcium carbonate-comprising filler material comprising at least one mono-substituted succinic anhydride and/or at least one mono-substituted succinic acid and/or salty reaction product(s) thereof in an amount of from 0.1 to 3 wt.-%, based on the total dry weight of the at least one calcium carbonate-comprising filler material.

21. The process of claim 20, wherein the composition provided in step a) is a masterbatch or a compound obtained by mixing and/or kneading the at least one thermoplastic polymer and the surface-treated filler material to form a mixture and continuously pelletizing the obtained mixture under water.

* * * * *